US006602659B1

(12) United States Patent
Waldman et al.

(10) Patent No.: US 6,602,659 B1
(45) Date of Patent: Aug. 5, 2003

(54) METHODS OF AND KITS AND COMPOSITIONS FOR DIAGNOSING COLORECTAL TUMORS AND METASTASIS THEREOF

(75) Inventors: Scott A. Waldman, Ardmore, PA (US); Stephen L. Carrithers, Lexington, KY (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/180,245

(22) PCT Filed: May 2, 1997

(86) PCT No.: PCT/US97/07467

§ 371 (c)(1),
(2), (4) Date: Mar. 11, 1999

(87) PCT Pub. No.: WO97/42506

PCT Pub. Date: Nov. 13, 1997

Related U.S. Application Data

(60) Provisional application No. 60/016,564, filed on May 3, 1996.

(51) Int. Cl.[7] ............... C12Q 1/68; G01N 33/48; C07K 14/435; C07K 14/705; C07H 21/04
(52) U.S. Cl. ............... 435/6; 436/64; 436/813; 530/350; 536/24.33
(58) Field of Search ............... 530/350; 435/6; 436/64, 813; 536/24.33

(56) References Cited

U.S. PATENT DOCUMENTS

| | | | |
|---|---|---|---|
| 4,584,268 A | 4/1986 | Ceriani et al. | 435/7 |
| 4,683,195 A | 7/1987 | Mullis et al. | 435/6 |
| 4,683,202 A | 7/1987 | Mullis | 435/91 |
| 4,965,188 A | 10/1990 | Mullis et al. | 435/6 |
| 5,075,216 A | 12/1991 | Innis et al. | 435/6 |
| 5,160,723 A | 11/1992 | Welt et al. | 424/1.1 |
| 5,237,051 A | 8/1993 | Garbers et al. | 530/350 |
| 5,518,888 A | 5/1996 | Waldman | 435/7.23 |
| 5,601,990 A | 2/1997 | Waldman | 435/7.23 |
| 5,731,159 A | 3/1998 | Waldman | 435/7.23 |

FOREIGN PATENT DOCUMENTS

WO     WO 95/11694     5/1995

OTHER PUBLICATIONS

Singh et al, "Isolation and expression of a guanylate cyclase–coupled heat stable enterotoxin receptor cDNA from a human colonic cell line", Biochemical and Biophysical Research Communications, vol. 179, pp. 1455–1463, Sep. 1991.*

Accession No. S57551, May 1993.* de Sauvage et al, "Primary Structure and functional Expression of the Human Receptor for *Escherichia coli* Heat–Stable Enterotoxin", Jounal of biological chemistry, vol. 266, No. 27, pp. 17912–17918, 1991.*

Carrithers et al, "*Escherichia coli* Heat–Stable Toxin Receptors in Human Colonic Tumors", Gastroenterology, vol. 107, No. 6, pp. 1653–1661, Dec. 1994.*

Hakki et al, "Solubilization and Characterization of Functionally Coupled *Escherichia coli* . . . ", Int. J. Biochem., vol. 25, No. 4, pp. 557–566, Apr. 1993.*

Noguchi et al, "The Detection of Breast Cacinoma Micrometastases in Axillary Lymph Nodes . . . ", Cancer, vol. 74, No. 5, pp. 1595–1600, Sep. 1994.*

Pearlman et al, "A Splice Variant of the Transcript for Guanylyl Cyclase C Is Expressed in Human Colon and colorectal Cancer Cells", Digestive Diseases and Sciences, vol. 45, No. 2, pp. 298–305, Feb. 2000.*

Hirayama et al, "Expression of a truncated guanylyl cyclase, a receptor for a heat–stable enterotoxin of . . . ", Microbial. Pathogenesis, vol. 15, No. 4, pp. 283–291, Oct. 1993.*

Ivans et al, "Heterogeneity of Intestinal Receptors for *Escherichia coli* Heat–Stable Endotoxin", Infection and Immunity, vol. 58, No. 6, pp. 1817–1820, 1990.*

Laney et al, "Novel sites for expression of an *Escherichia coli* heat–stable enterotoxin receptor in the developong rat", American J of Physiology, vol. 263, No. 5, Pt. 1, pp. G816–821, 1992.*

Almenoff et al, "Induction of Heat–stable Enterotoxin Receptor Activity by a Human Alu Repeat", Journal of Biological Chemistry, vol. 269, No. 24, pp. 16610–16617, Jun. 1994.*

Singh et al, "Isolation and Expression of a Guanylyl Cyclase Coupled Heat Stable Enterotoxin Receptor cDNA from a Human Colonic Cell Line", Biochem and Biophys Res Comm, vol. 179, No. 3, pp. 1455–1463, 1991.*

Krause et al, "Distribution of membrane bound guanylyl cyclases in human intestine", Gut, vol. 35, No. 9, pp. 1250–1257, Sep. 1994.*

Coperhave et al., "The Digestive System", *Bailey's Textbook of Histology*, 16th Edition, Williams and Wilkens, Baltimore, MD, 1975, p. 404.

de Savauge, et al., "Primary Structure and Functional Expression of the Human Receptor for *Escherichia coli* Heat–stable Enterotoxin", *J. Biol. Chem.*, 1991, 266, 17912–17918.

(List continued on next page.)

Primary Examiner—Anthony C. Caputa
Assistant Examiner—Karen A. Canella
(74) Attorney, Agent, or Firm—Woodcock Washburn LLP

(57) ABSTRACT

In vitro methods of determining whether or not an individual has metastasized colorectal cancer cells are disclosed. In vitro methods of determining whether or not tumor cells are colorectal in origin are disclosed. In vitro kits for practicing the methods of the invention and to reagents and compositions useful to practice the methods, for example as components in such in vitro kits of the invention are provided. Methods of and kits and compositions for analyzing tissue samples from the colon tissue to evaluate the extent of metastasis of colorectal tumor cells are disclosed.

12 Claims, No Drawings

OTHER PUBLICATIONS

Wide, L., "Solid Phase Antigen–Antibody Systems", in *Radioimmunoassay Method*, Kirkham, Ed., E. & S. Livingston, eds., Edinburgh, 1970, pp. 405–413.

Almenoff, et al., "Ligand–based Histochemical Localization and Capture of Cells Expressing Heat–Stable Enterotoxin Receptors", *Molecular Microbiology*, 1993, 8, 865–873.

Bjorn, et al., "Antibody–Pseudomonas Exotoxin A Conjugates Cytotoxic to Human Breast Cancer Cells In Vitro", *Cancer Research*, 1986, 46, 3262–3267.

Bjorn, et al., "Evaluation of Monoclonal Antibodies for the Development of Breast Cancer Immunotoxins", *Cancer Research*, 1985, 45, 1214–1221.

Burgess, et al., "Biological Evaluation of a Methanol–Soluble, Heat–Stable *Escherichia coli* Enterotoxin in Infant Mice, Pigs, Rabbits and Calves", *Infection and Immunity*, 1978, 21, 526–531.

Cawley and Herschman, "Epidermal Growth Factor–Toxin A Chain Conjugates: EGF–Ricin A is a Potent Toxin While EGF–Diphtheria Fragment A is Nontoxic", *Cell*, 1980, 22, 563–570.

Ceriani, R., et al., "Variability in Surface Antigen Expression of Human Breast Epithelial Cells Cultured from Normal Breast, Normal Tissue Peripheral to Breast Carcinomas, and Breast Carcinomas", *Cancer Res.*, Jul., 1984, 44, 3033–3039.

Ceriani, R., et al., "Circulating Human Mammary Epithelial Antigens in Breast Cancer", *PNAS USA*, 1982, 79, 5420–5424.

Chan and Giannella, "Amino Acid Sequence of Heat–stable Enterotoxin Produced by *Escherichia coli* Pathogenic for Man", *J. Biol. Chem.*, 1981, 256, 7744–7746.

Chung and Collier, "Enzymatically Active Peptide from the Adenosine Dithosphate–Ribosylating Toxin of *Pseudomonas aeruginosa*", 1977, 16, 832–841.

Cohen, M., et al., "Receptors for *Escherichia coli* Heat Stable Enterotoxin in Human Intestine and in a Human Intestinal Cell Line (Caco–2)", *J. Of Cellular Physiol*, 1993, 156, 138–144.

Corstens, F. And van der Meer, Jos. W.M., Chemotactic peptides: New Locomotion for Imaging of Infection?, *J. Nucl. Med.*, 1991, 32(3), 491–494.

Cumber, et al., "Preparation of Antibody–Toxin Conjugates", *Methods in Enzymology*, 1985, 112, 207–225.

Currie, et al., "Guanylin: An endogenous Activator of Intestinal Guanylate Cyclase", *Proc. Natl. Acad. Sci. USA*, 1992, 89, 947–951.

Dreyfus, et al., "Chemical Properties of Heat–Stable Enterotoxins Produced by Interotoxigenic *Escherichia coli* of Different Host Origins", *Infection and Immunity*, 1983, 42, 539–548.

Drewett, J. And Garbers, "The Family of Guanylyl Cyclase Receptors and Their Ligands", *Endocrine Reviews*, 1994, 15(2), 135–162.

Eckelman, et al., "Comparison of $^{99m}$Tc and $^{111}$In Labeling of Conjugated Antibodies", *Nucl. Med. Biol.*, 1986, 13, 335–343.

Evans, et al., "Different in the Response of Rabbit Small Intestine to Heat–Labile and Heat–Stable Enterotoxins of *Escherichia coli*", *Infection and Immunity*, 1973, 7, 873–880.

Fischman, Alan. J., et al., "A Ticket to Ride: Peptide Radiopharmaceuticals", *J. Nucl. Med.*, 1993, 34(12), 2253–2263.

Fitzgerald, et al., "Adenovirus–Induced Release of Epidermal Growth Factor and pseudomonas Toxin into the Cytosol of KB Cells during Receptor–Mediated Endocytosis", *Cell*, 1983, 32, 607–617.

Fitzgerald, et al., "Construction of Immunotoxins Using Pseudomonas Exotoxin A", *Methods in Enzymology*, 1987, 151, 139–145.

Forte, L., et al., "Receptors and cGMP Signaling Mechanism for *E. coli* Enterotoxin in Opossum Kidney", Am. J. *Physiol.*, 1988, 255 (5 Pt. 2), F1040–F1046.

Forte, L., et al., "*Escherichia coli* Enterotoxin Receptors: Localization in Opossum Kidney, Intestine, and Testis", *Am. J. Physiol.*, 1989, 257 (Pt. 2), F874–881.

Forte, L., et al., "Guanylin: A Peptide Regulator of Epithelial Transport", *FASEB J*, 1995, 9, 643–650.

Giannella, et al., "Development of a Radioimmunoassay for *Escherichia coli* Heat–Stable Enterotoxin: Comparison with the Suckling mouse Bioassay", *Infection and Immunity*, 1981, 33, 186–192.

Gros, O., "Biochemical Aspects of Immunotoxin Preparation", *J. Immunol. Meth.*, 1985, 81, 283–297.

Guarino, A., et al., "$T^{84}$, Cell Receptor Binding and Guanyl Cyclas Activation by *Escherichia coli* Heat–Stable Toxin", *Am. J. Physiol*, 253 (Gastrointest. Liver Physiol. 16): G775–780, 1987.

Guerrant, R., et al., "Activation of Intestinal Guanylate Cyclase by Heat–Stable Enterotoxin of *Escherichia coli*: Studies of tissue Specificity, Potential Receptors, and Intermediates", *J. Infect. Dis.*, 1980, 142(2), 220–228.

Gyles, C.L., "Discussion Heat–Labile and Heat–Stable Forms of the Enterotoxin from *E. coli* Strains Enteropathogenic for Pigs", *Ann. N.Y. Acad. Sci.*, 1979, 16, 314–321.

Hakki, et al., "Solubilization and Characterization of Functionally Coupled *Escherichia coli* Heat–Stable Toxin Receptors and Particulate Guanylate Cyclase Associated with the Cytoskeleton Compartment of Intestinal Membranes", *Int. J. Biochem.*, 1993, 25, 557–566.

Hardingham, J.E., et al., "Immunobead–PCR: A Technique for the Detection of Circulating Tumor Cells Using Immunomagnetic Beads and the Polymerase Chain Reaction", *Cancer Research*, 1993, 53, 3455–3458.

Hugues, et al., "Identification and Characterization of a New Family of High–Affinity Receptors for *Escherichia coli* Heat–Stable Enterotoxin in Rat Intestinal Membranes", *Biochemistry*, 1991, 30, 10738–10745.

Humm, et al., "Dosimetric Aspects of Radiolabeled Antibodies for Tumor Therapy", *J. Nuclear Med.*, 1986, 27, 1490–1497.

Klipstein, et al., "Development of a Vaccine of Cross–Linked Heat–Stable and Heat–Labile Enterotoxins that Protets Against *Escherichia coli* Producing Either Enterotoxin", *Infection and Immunity*, 1982, 37, 550–557.

Krause, W., et al., "Autoradiographic Demonstration of Specific Binding Sites for *E. coli* Enterotoxin in Various Epithelia of the North American Oppossum", *Cell Tissue Res.*, 1990, 260, 387–394.

Krejcarek and Tucker, "Covalent Attachment of Chelating Groups to Macromolecules", *Biochemical and Biophysical Research Communications*, 1977, 77, 581–585.

Kwok, "Calculation of Radiation Doses for Nonuniformly Distributed β and γ Radionuclides in Soft Tissue", *Med. Phys.*, 1985, 12, 405–412.

Leonard, et al., "Kinetics of Protein Synthesis Inactivation in Human T–Lymphocytes by Selective Monoclonal Antibody–Ricin Conjugates", *Cancer Research*, 1985, 45, 5263–5269.

Lima, A., et al., "The Effects of *Escherichia coli* Heat–Stable Enterotoxin in Renal Sodium Tubular Transport", *Pharmacology & Toxicology*, 1992, 70, 163–167.

Magerstadt, M., et al. "Antibody Conjugates and Malignant Disease", CRC Press, Boca Raton, 1991, 42–45 and 110–152.

Masuho, et al., "Importance of the Antigen–Binding Valency and the Nature of the Cross–Linking Bond in Ricin A–Chain Conjugates with Antibody", *J. Biochem.*, 1982, 91, 1583–1591.

Merrifield, "Solid Phase Peptide Synthesis. I. The Synthesis of a Tetrapeptide", *J. Am. Chem., Soc.*, 1963, 85, 2149–2154.

Michel and Dirkx, "Fluorescence Studies of Nucleotides Binding to Diphtheria Toxin and Its Fragment A", *Biochimica et Biophysia Acta*, 1974, 365, 15–27.

Moseley, et al., "Isolation and Nucleotide Sequence Determination of a Gene Encoding a Heat–Stable Enterotoxin of *Escherichia col*", *Infection and Immunity*, 1983, 39, 1167–1174.

Okamoto, et al., "Substitutions of Cysteine Residues of *Escherichia coli* Heat–Stable Enterotoxin By Oligonucleotide–Directed Mutagenesis", *Infection and Immunity*, 1987, 55, 2121–2125.

Rao, M., et al., "Mode of Action of Heat–Stable *Escherichia coli* Enterotoxin Tissue and Subcellular specificities and Role of Cyclic GMP", *Biochimica et Biophysica Acta*, 1980, 632, 35–46.

Richardson, et al., "Astatine ($^{211}$At) as a Therapeutic Radionuclide. The Plasma: Blood Cell Distribution in Vitro", *Nucl. Med. Biol.*, 1986, 13, 583–584.

Sack, "Human Diarrheal Disease Caused by Enterotoxigenic *Escherichia coli*", *Ann. Rev. Microbiol.*, 1975, 29, 333–353.

Schulz, S., et al., "Cloning and Expression of Guanylin", *The J. Of Biological Chem.*, 1992, 267(23), 16019–16021.

Shimonishi, et al., "Mode of Disulfide Bond Formation of a Heat–Stable Enterotoxin ($ST_h$) Produced by a Human Strain of Enterotoxigenic *Escherichia coli*", *FEBS Letters*, 1987, 215, 165–170.

So and McCarthy, "Nucleotide Sequence of the Bacterial Thansposon Tn1681 Encoding a Heat–Stable (ST) Toxin and Its Identification in Enterotoxigenic *Escherichia coli* Strains", *Proc. Natl. Acad. Sci. USA*, 1980, 77, 4011–4015.

Spitler, et al., "Therapy of Patients with Malignant Melanoma Using a Monoclonal Antimelanoma Antibody–Ricin A Chain Immunotoxin", *Cancer Research*, 1987, 47, 1717–1723.

Steinstraβer, et al., "Selection of Nuclides for Immunoscintigraphy/Immunotherapy", *J. Nucl. Med.*, 1988, 5, 875.

Thompson, et al., "Biological and Immunological Characteristics of$^{125}$I–4Tyr and—18Tyr *Escherichia coli* Heat–Stable Enterotoxin Species Purified by High–Performance Liquid Chromatography", *Analytical Biochemistry*, 1985, 148, 26–36.

Thompson, M.R., "*Escherichia coli* Heat–Stable Enterotoxins and Their Receptors", *Pathol. Immunopathol. Res.*, 1987, 6, 103–116.

Thorpe, et al., "New Coupling Agents for the Synthesis of Immunotoxins Containing a Hindered Disulfide Bond with Improved Stability In Vivo", Cancer Research, 1987, 47, 5924–5931.

Vaandrager, A., et al., "Atriopeptins and *Escherichia coli* Enterotoxin $ST^a$ Have Different Sites of Action in Mammalian Intestine", *Gastroenterology*, 1992, 102(4), 1161–1169.

Waldman and O'Hanley, "Influence of a Glycine or Proline Substitution on the Functional Properties of a 14–Amino–Acid Analog of *Escherichia coli* Heat–Stable Enterotoxin", *Infection and Immunity*, 1989, 57, 2420–2424.

Wessels and Rogus, "Radionuclide Selection and Model Absorbed Dose Calculations for Radiolabeled Tumor Associated Antibodies", *Med. Phys.* 1984, 11, 638–645.

White, A., et al., "Opossum Kidney Contains a Functional Receptor for the *Escherichia coli* Heat–Stable Enterotoxin", *Biochemical and Biophysical Res. Comm.*, 1989, 159(1), 363–367.

Worrell, et al., "Effect of Linkage Variation on Pharmacokinetics of Ricin A Chain–Antibody Conjugates in Normal Rats", *Anti–Cancer Drug Design*, 1986, 1, 179–188.

Yoshimura, et al., "Essential Stucture for Full Interotoxigenic Activity of Heat–Stable Enterotoxin Produced by Enterotoxigenic *Escherichia coli*", *FEBS* 2232, 1985, 181, 138–142.

Bodansky, et al., "Peptide Synthesis", John Wiley & Sons, 2d. Ed., (1976).

Franz, et al., "The Production of $^{99m}$Tc–Labeled Conjugated Antibodies Using A Cyclam–Based Bifunctional Chelating Agent", *J. Nucl. Med. Biol.*, 1987, 14, 569–572.

Vaandrager, A. et al., *J. Biol. Chem.*, Jan. 25, 1993, 268(3), 2174–2179 (Abstract Only).

Aitken, R. et al., "Recombinant enterotoxins as vaccines against *Escherichia coli*–mediated diarrhoea", *Vaccine*, 1993, 11(2), 227–233.

Chelly, J. et al., "Illegitimate transcription: Transcription of any gene in any cell type", *Proc. Natl. Acad. Sci. USA*, 1989, 86, 2617–2621.

Chelly, J. et al., "Illegitimate Transcription: Application to the Analysis of Truncated Transcripts of the Dystrophin Gene in Nonmuscle Cultured Cells from Duchenne and Becker Patients", *J. Clin. Invest.*, 1991, 88(4), 1161–1166.

Cooper, D.N. et al., "Ectopic (Illegitimate) Transcription: New Possibilities for the Analysis and Diagnosis of Human Genetic Disease", *Ann. Med.*, 1994, 26(1), 9–14.

Field, M., "Role of Cyclic Nucleotides in Enterotoxic Diarrhea", *Mol. Cyclic Nucl. Res.*, 1980, 12, 267–277.

Giannella, R.A., "Pathogenesis of Acute Bacterial Diarrheal Disorders", *Ann. Rev. Med.*, 1981, 32, 341–357.

Kaplan, J.C. et al., "Illegitimate transcription: its use in the study of inherited disease", *Human Mutation*, 1992, 1(5), 357–360 (Abstract only).

Negrier, C. et al., "Illegitimate transcription: its use for studying genetic abnormalities in lymphoblastoid cells from patients with *Glanzmann thrombasthenia*", *British J. Haematology*, 1998, 100(1), 33–39.

Rao, M.C. et al., "Enterotoxins and Anti–toxins: Enterotoxins and ion transport", *Biochem.*, 1984, 12, 177–180.

Zippelius, A. et al., "Limitations of Reverse–Transcriptase Polymerase Chain Reaction Analyses for Detection of Micrometastatic Epithelial Cancer Cells in Bone Marrow", *J. Clin. Oncology*, 1997, 15(7), 2701–2708.

* cited by examiner

SEQUENCE LISTING

```
<160> NUMBER OF SEQ ID NOS: 74

<210> SEQ ID NO 1
<211> LENGTH: 3786
<212> TYPE: DNA
<213> ORGANISM: Homo sapiens
<220> FEATURE:
<221> NAME/KEY: CDS
<222> LOCATION: (118)..(3339)
<220> FEATURE:
<223> OTHER INFORMATION: Extracellular domain - nucleotides 187-1407,
      corresponding to amino acids 24-430.
<220> FEATURE:
<223> OTHER INFORMATION: Carboxy terminal tail - nucleotides 3148-3336,
      corresponding to amino acids 1011-1073.

<400> SEQUENCE: 1
tggagtgggc tgagggactc cactagaggc tgtccatctg gattccctgc ctccctagga      60
gcccaacaga gcaaagcaag tgggcacaag gagtatggtt ctaacgtgat tggggtc        117 atg aag acg ttg ctg ttg gac ttg gct ttg tgg tca ctg ctc ttc cag       165
Met Lys Thr Leu Leu Leu Asp Leu Ala Leu Trp Ser Leu Leu Phe Gln
  1               5                  10                  15
```

```
ccc ggg tgg ctg tcc ttt agt tcc cag gtg agt cag aac tgc cac aat        213
Pro Gly Trp Leu Ser Phe Ser Ser Gln Val Ser Gln Asn Cys His Asn
             20                  25                  30 ggc agc tat gaa atc agc gtc ctg atg atg ggc aac tca gcc ttt gca        261
Gly Ser Tyr Glu Ile Ser Val Leu Met Met Gly Asn Ser Ala Phe Ala
         35                  40                  45 gag ccc ctg aaa aac ttg gaa gat gcg gtg aat gag ggg ctg gaa ata        309
Glu Pro Leu Lys Asn Leu Glu Asp Ala Val Asn Glu Gly Leu Glu Ile
     50                  55                  60 gtg aga gga cgt ctg caa aat gct ggc cta aat gtg act gtg aac gct        357
Val Arg Gly Arg Leu Gln Asn Ala Gly Leu Asn Val Thr Val Asn Ala
 65                  70                  75                  80 act ttc atg tat tcg gat ggt ctg att cat aac tca ggc gac tgc cgg        405
Thr Phe Met Tyr Ser Asp Gly Leu Ile His Asn Ser Gly Asp Cys Arg
                 85                  90                  95 agt agc acc tgt gaa ggc ctc gac cta ctc agg aaa att tca aat gca        453
Ser Ser Thr Cys Glu Gly Leu Asp Leu Leu Arg Lys Ile Ser Asn Ala
            100                 105                 110 caa cgg atg ggc tgt gtc ctc ata ggg ccc tca tgt aca tac tcc acc        501
Gln Arg Met Gly Cys Val Leu Ile Gly Pro Ser Cys Thr Tyr Ser Thr
        115                 120                 125 ttc cag atg tac ctt gac aca gaa ttg agc tac ccc atg atc tca gct        549
Phe Gln Met Tyr Leu Asp Thr Glu Leu Ser Tyr Pro Met Ile Ser Ala
    130                 135                 140 gga agt ttt gga ttg tca tgt gac tat aaa gaa acc tta acc agg ctg        597
Gly Ser Phe Gly Leu Ser Cys Asp Tyr Lys Glu Thr Leu Thr Arg Leu
145                 150                 155                 160 atg tct cca gct aga aag ttg atg tac ttc ttg gtt aac ttt tgg aaa        645
Met Ser Pro Ala Arg Lys Leu Met Tyr Phe Leu Val Asn Phe Trp Lys
                165                 170                 175 acc aac gat ctg ccc ttc aaa act tat tcc tgg agc act tcg tat gtt        693
Thr Asn Asp Leu Pro Phe Lys Thr Tyr Ser Trp Ser Thr Ser Tyr Val
            180                 185                 190 tac aag aat ggt aca gaa act gag gac tgt ttc tgg tac ctt aat gct        741
Tyr Lys Asn Gly Thr Glu Thr Glu Asp Cys Phe Trp Tyr Leu Asn Ala
        195                 200                 205 ctg gag gct agc gtt tcc tat ttc tcc cac gaa ctc ggc ttt aag gtg        789
Leu Glu Ala Ser Val Ser Tyr Phe Ser His Glu Leu Gly Phe Lys Val
    210                 215                 220 gtg tta aga caa gat aag gag ttt cag gat atc tta atg gac cac aac        837
Val Leu Arg Gln Asp Lys Glu Phe Gln Asp Ile Leu Met Asp His Asn
225                 230                 235                 240 agg aaa agc aat gtg att att atg tgt ggt ggt cca gag ttc ctc tac        885
Arg Lys Ser Asn Val Ile Ile Met Cys Gly Gly Pro Glu Phe Leu Tyr
                245                 250                 255 aag ctg aag ggt gac cga gca gtg gct gaa gac att gtc att att cta        933
Lys Leu Lys Gly Asp Arg Ala Val Ala Glu Asp Ile Val Ile Ile Leu
            260                 265                 270 gtg gat ctt ttc aat gac cag tac ttg gag gac aat gtc aca gcc cct        981
Val Asp Leu Phe Asn Asp Gln Tyr Leu Glu Asp Asn Val Thr Ala Pro
        275                 280                 285 gac tat atg aaa aat gtc ctt gtt ctg acg ctg tct cct ggg aat tcc       1029
Asp Tyr Met Lys Asn Val Leu Val Leu Thr Leu Ser Pro Gly Asn Ser
    290                 295                 300 ctt cta aat agc tct ttc tcc agg aat cta tca cca aca aaa cga gac       1077
Leu Leu Asn Ser Ser Phe Ser Arg Asn Leu Ser Pro Thr Lys Arg Asp
305                 310                 315                 320 ttt cgt ctt gcc tat ttg aat gga atc ctc gtc ttt gga cat atg ctg       1125
Phe Arg Leu Ala Tyr Leu Asn Gly Ile Leu Val Phe Gly His Met Leu
                325                 330                 335
```

```
aag ata ttt ctt gaa aat gga gaa aat att acc acc ccc aaa ttt gct    1173
Lys Ile Phe Leu Glu Asn Gly Glu Asn Ile Thr Thr Pro Lys Phe Ala
            340                 345                 350 cat gcc ttc agg aat ctc act ttt gaa ggg tat gac ggt cca gtg acc    1221
His Ala Phe Arg Asn Leu Thr Phe Glu Gly Tyr Asp Gly Pro Val Thr
                355                 360                 365 ttg gat gac tgg ggg gat gtt gac agt acc atg gtg ctt ctg tat acc    1269
Leu Asp Asp Trp Gly Asp Val Asp Ser Thr Met Val Leu Leu Tyr Thr
370                 375                 380 tct gtg gac acc aag aaa tac aag gtt ctt ttg acc tat gat acc cac    1317
Ser Val Asp Thr Lys Lys Tyr Lys Val Leu Leu Thr Tyr Asp Thr His
385                 390                 395                 400 gta aat aag acc tat cct gtg gat atg agc ccc aca ttc act tgg aag    1365
Val Asn Lys Thr Tyr Pro Val Asp Met Ser Pro Thr Phe Thr Trp Lys
                405                 410                 415 aac tct aaa ctt cct aat gat att aca ggc cgg ggc cct cag atc ctg    1413
Asn Ser Lys Leu Pro Asn Asp Ile Thr Gly Arg Gly Pro Gln Ile Leu
                420                 425                 430 atg att gca gtc ttc acc ctc act gga gct gtg gtg ctg ctc ctg ctc    1461
Met Ile Ala Val Phe Thr Leu Thr Gly Ala Val Val Leu Leu Leu Leu
                435                 440                 445 gtc gct ctc ctg atg ctc aga aaa tat aga aaa gat tat gaa ctt cgt    1509
Val Ala Leu Leu Met Leu Arg Lys Tyr Arg Lys Asp Tyr Glu Leu Arg
450                 455                 460 cag aaa aaa tgg tcc cac att cct cct gaa aat atc ttt cct ctg gag    1557
Gln Lys Lys Trp Ser His Ile Pro Pro Glu Asn Ile Phe Pro Leu Glu
465                 470                 475                 480 acc aat gag acc aat cat gtt agc ctc aag atc gat gat gac aaa aga    1605
Thr Asn Glu Thr Asn His Val Ser Leu Lys Ile Asp Asp Asp Lys Arg
                485                 490                 495 cga gat aca atc cag aga cta cga cag tgc aaa tac gtc aaa aag cga    1653
Arg Asp Thr Ile Gln Arg Leu Arg Gln Cys Lys Tyr Val Lys Lys Arg
                500                 505                 510 gtg att ctc aaa gat ctc aag cac aat gat ggt aat ttc act gaa aaa    1701
Val Ile Leu Lys Asp Leu Lys His Asn Asp Gly Asn Phe Thr Glu Lys
                515                 520                 525 cag aag ata gaa ttg aac aag ttg ctt cag att gac tat tac acc cta    1749
Gln Lys Ile Glu Leu Asn Lys Leu Leu Gln Ile Asp Tyr Tyr Thr Leu
                530                 535                 540 acc aag ttc tac ggg aca gtg aaa ctg gat acc atg atc ttc ggg gtg    1797
Thr Lys Phe Tyr Gly Thr Val Lys Leu Asp Thr Met Ile Phe Gly Val
545                 550                 555                 560 ata gaa tac tgt gag aga gga tcc ctc cgg gaa gtt tta aat gac aca    1845
Ile Glu Tyr Cys Glu Arg Gly Ser Leu Arg Glu Val Leu Asn Asp Thr
                565                 570                 575 att tcc tac cct gat ggc aca ttc atg gat tgg gag ttt aag atc tct    1893
Ile Ser Tyr Pro Asp Gly Thr Phe Met Asp Trp Glu Phe Lys Ile Ser
                580                 585                 590 gtc ttg tat gac att gct aag gga atg tca tat ctg cac tcc agt aag    1941
Val Leu Tyr Asp Ile Ala Lys Gly Met Ser Tyr Leu His Ser Ser Lys
                595                 600                 605 aca gaa gtc cat ggt cgt ctg aaa tct acc aac tgc gta gtg gac agt    1989
Thr Glu Val His Gly Arg Leu Lys Ser Thr Asn Cys Val Val Asp Ser
                610                 615                 620 aga atg gtg gtg aag atc act gat ttt ggc tgc aat tcc att ttg cct    2037
Arg Met Val Val Lys Ile Thr Asp Phe Gly Cys Asn Ser Ile Leu Pro
625                 630                 635                 640 cca aaa aag gac ctg tgg aca gct cca gag cac ctc cgc caa gcc aac    2085
Pro Lys Lys Asp Leu Trp Thr Ala Pro Glu His Leu Arg Gln Ala Asn
```

-continued

| | | | |
|---|---|---|---|
| 645 | 650 | 655 | |
| atc tct cag aaa gga gat gtg tac agc tat ggg atc atc gca cag gag<br>Ile Ser Gln Lys Gly Asp Val Tyr Ser Tyr Gly Ile Ile Ala Gln Glu<br>660 665 670 | | | 2133 |
| atc att ctg cgg aaa gaa acc ttc tac act ttg agc tgt cgg gac cgg<br>Ile Ile Leu Arg Lys Glu Thr Phe Tyr Thr Leu Ser Cys Arg Asp Arg<br>675 680 685 | | | 2181 |
| aat gag aag att ttc aga gtg gaa aat tcc aat gga atg aaa ccc ttc<br>Asn Glu Lys Ile Phe Arg Val Glu Asn Ser Asn Gly Met Lys Pro Phe<br>690 695 700 | | | 2229 |
| cgc cca gat tta ttc ttg gaa aca gca gag gaa aaa gag cta gaa gtg<br>Arg Pro Asp Leu Phe Leu Glu Thr Ala Glu Glu Lys Glu Leu Glu Val<br>705 710 715 720 | | | 2277 |
| tac cta ctt gta aaa aac tgt tgg gag gaa gat cca gaa aag aga cca<br>Tyr Leu Leu Val Lys Asn Cys Trp Glu Glu Asp Pro Glu Lys Arg Pro<br>725 730 735 | | | 2325 |
| gat ttc aaa aaa att gag act aca ctt gcc aag ata ttt gga ctt ttt<br>Asp Phe Lys Lys Ile Glu Thr Thr Leu Ala Lys Ile Phe Gly Leu Phe<br>740 745 750 | | | 2373 |
| cat gac caa aaa aat gaa agc tat atg gat acc ttg atc cga cgt cta<br>His Asp Gln Lys Asn Glu Ser Tyr Met Asp Thr Leu Ile Arg Arg Leu<br>755 760 765 | | | 2421 |
| cag cta tat tct cga aac ctg gaa cat ctg gta gag gaa agg aca cag<br>Gln Leu Tyr Ser Arg Asn Leu Glu His Leu Val Glu Glu Arg Thr Gln<br>770 775 780 | | | 2469 |
| ctg tac aag gca gag agg gac agg gct gac aga ctt aac ttt atg ttg<br>Leu Tyr Lys Ala Glu Arg Asp Arg Ala Asp Arg Leu Asn Phe Met Leu<br>785 790 795 800 | | | 2517 |
| ctt cca agg cta gtg gta aag tct ctg aag gag aaa ggc ttt gtg gag<br>Leu Pro Arg Leu Val Val Lys Ser Leu Lys Glu Lys Gly Phe Val Glu<br>805 810 815 | | | 2565 |
| ccg gaa cta tat gag gaa gtt aca atc tac ttc agt gac att gta ggt<br>Pro Glu Leu Tyr Glu Glu Val Thr Ile Tyr Phe Ser Asp Ile Val Gly<br>820 825 830 | | | 2613 |
| ttc act act atc tgc aaa tac agc acc ccc atg gaa gtg gtg gac atg<br>Phe Thr Thr Ile Cys Lys Tyr Ser Thr Pro Met Glu Val Val Asp Met<br>835 840 845 | | | 2661 |
| ctt aat gac atc tat aag agt ttt gac cac att gtt gat cat cat gat<br>Leu Asn Asp Ile Tyr Lys Ser Phe Asp His Ile Val Asp His His Asp<br>850 855 860 | | | 2709 |
| gtc tac aag gtg gaa acc atc ggt gat gcg tac atg gtg gct agt ggt<br>Val Tyr Lys Val Glu Thr Ile Gly Asp Ala Tyr Met Val Ala Ser Gly<br>865 870 875 880 | | | 2757 |
| ttg cct aag aga aat ggc aat cgg cat gca ata gac att gcc aag atg<br>Leu Pro Lys Arg Asn Gly Asn Arg His Ala Ile Asp Ile Ala Lys Met<br>885 890 895 | | | 2805 |
| gcc ttg gaa atc ctc agc ttc atg ggg acc ttt gag ctg gag cat ctt<br>Ala Leu Glu Ile Leu Ser Phe Met Gly Thr Phe Glu Leu Glu His Leu<br>900 905 910 | | | 2853 |
| cct ggc ctc cca ata tgg att cgc att gga gtt cac tct ggt ccc tgt<br>Pro Gly Leu Pro Ile Trp Ile Arg Ile Gly Val His Ser Gly Pro Cys<br>915 920 925 | | | 2901 |
| gct gct gga gtt gtg gga atc aag atg cct cgt tat tgt cta ttt gga<br>Ala Ala Gly Val Val Gly Ile Lys Met Pro Arg Tyr Cys Leu Phe Gly<br>930 935 940 | | | 2949 |
| gat acg tca aac aca gcc tct agg atg gaa tcc act ggc ctc cct ttg<br>Asp Thr Val Asn Thr Ala Ser Arg Met Glu Ser Thr Gly Leu Pro Leu<br>945 950 955 960 | | | 2997 |
| aga att cac gtg agt ggc tcc acc ata gcc atc ctg aag aga act gag | | | 3045 |

```
Arg Ile His Val Ser Gly Ser Thr Ile Ala Ile Leu Lys Arg Thr Glu
                965                 970                 975 tgc cag ttc ctt tat gaa gtg aga gga gaa aca tac tta aag gga aga    3093
Cys Gln Phe Leu Tyr Glu Val Arg Gly Glu Thr Tyr Leu Lys Gly Arg
            980                 985                 990 gga aat gag act acc tac tgg ctg act ggg atg aag gac cag aaa ttc    3141
Gly Asn Glu Thr Thr Tyr Trp Leu Thr Gly Met Lys Asp Gln Lys Phe
        995                 1000                1005 aac ctg cca acc cct cct act gtg gag aat caa cag cgt ttg caa gca    3189
Asn Leu Pro Thr Pro Pro Thr Val Glu Asn Gln Gln Arg Leu Gln Ala
    1010                1015                1020 gaa ttt tca gac atg att gcc aac tct tta cag aaa aga cag gca gca    3237
Glu Phe Ser Asp Met Ile Ala Asn Ser Leu Gln Lys Arg Gln Ala Ala
1025                1030                1035                1040 ggg ata aga agc caa aaa ccc aga cgg gta gcc agc tat aaa aaa ggc    3285
Gly Ile Arg Ser Gln Lys Pro Arg Arg Val Ala Ser Tyr Lys Lys Gly
                1045                1050                1055 act ctg gaa tac ttg cag ctg aat acc aca gac aag gag agc acc tat    3333
Thr Leu Glu Tyr Leu Gln Leu Asn Thr Thr Asp Lys Glu Ser Thr Tyr
            1060                1065                1070 ttt taa acctaaatga ggtataagga ctcacacaaa ttaaaataca gctgcactga     3389
Phe ggccaggcac cctcaggtgt cctgaaagct tactttcctg agacctcatg aggcagaaat  3449
gtcttaggct tggctgccct gtttggacca tggactttct ttgcatgaat cagatgtgtt  3509
ctcagtgaaa taactacctt ccactctgga accttattcc agcagttgtt ccagggagct  3569
tctacctgga aaagaaaaga atttcattta ttttttgttt gtttattttt atcgtttttg  3629
tttactggct ttccttctgt attcataaga ttttttaaat tgtcataatt atattttaaa  3689
tacccatctt cattaaagta tatttaactc ataattttg cagaaaatat gctatatatt   3749
aggcaagaat aaaagctaaa ggtttcccaa aaaaaaa                           3786

<210> SEQ ID NO 2
<211> LENGTH: 1073
<212> TYPE: PRT
<213> ORGANISM: Homo sapiens
<220> FEATURE:
<223> OTHER INFORMATION: Carboxy terminal tail - nucleotides 3148-3336,
      corresponding to amino acids 1011-1073.

<400> SEQUENCE: 2

Met Lys Thr Leu Leu Asp Leu Ala Leu Trp Ser Leu Leu Phe Gln
  1               5                  10                  15

Pro Gly Trp Leu Ser Phe Ser Ser Gln Val Ser Gln Asn Cys His Asn
             20                  25                  30

Gly Ser Tyr Glu Ile Ser Val Leu Met Met Gly Asn Ser Ala Phe Ala
         35                  40                  45

Glu Pro Leu Lys Asn Leu Glu Asp Ala Val Asn Glu Gly Leu Glu Ile
     50                  55                  60

Val Arg Gly Arg Leu Gln Asn Ala Gly Leu Asn Val Thr Val Asn Ala
 65                  70                  75                  80

Thr Phe Met Tyr Ser Asp Gly Leu Ile His Asn Ser Gly Asp Cys Arg
                 85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125
```

```
Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
                180                 185                 190

Tyr Lys Asn Gly Thr Glu Thr Glu Asp Cys Phe Trp Tyr Leu Asn Ala
            195                 200                 205

Leu Glu Ala Ser Val Ser Tyr Phe Ser His Glu Leu Gly Phe Lys Val
        210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
                260                 265                 270

Val Asp Leu Phe Asn Asp Gln Tyr Leu Glu Asp Asn Val Thr Ala Pro
            275                 280                 285

Asp Tyr Met Lys Asn Val Leu Val Leu Thr Leu Ser Pro Gly Asn Ser
        290                 295                 300

Leu Leu Asn Ser Ser Phe Ser Arg Asn Leu Ser Pro Thr Lys Arg Asp
305                 310                 315                 320

Phe Arg Leu Ala Tyr Leu Asn Gly Ile Leu Val Phe Gly His Met Leu
                325                 330                 335

Lys Ile Phe Leu Glu Asn Gly Glu Asn Ile Thr Thr Pro Lys Phe Ala
                340                 345                 350

His Ala Phe Arg Asn Leu Thr Phe Glu Gly Tyr Asp Gly Pro Val Thr
            355                 360                 365

Leu Asp Asp Trp Gly Asp Val Asp Ser Thr Met Val Leu Leu Tyr Thr
        370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Gln Ile Leu
                420                 425                 430

Met Ile Ala Val Phe Thr Leu Thr Gly Ala Val Val Leu Leu Leu Leu
            435                 440                 445

Val Ala Leu Leu Met Leu Arg Lys Tyr Arg Lys Asp Tyr Glu Leu Arg
        450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
                485                 490                 495

Arg Asp Thr Ile Gln Arg Leu Arg Gln Cys Lys Tyr Val Lys Lys Arg
                500                 505                 510

Val Ile Leu Lys Asp Leu Lys His Asn Asp Gly Asn Phe Thr Glu Lys
            515                 520                 525

Gln Lys Ile Glu Leu Asn Lys Leu Leu Gln Ile Asp Tyr Tyr Thr Leu
        530                 535                 540

Thr Lys Phe Tyr Gly Thr Val Lys Leu Asp Thr Met Ile Phe Gly Val
```

```
                                      -continued
545                  550                 555                 560

Ile Glu Tyr Cys Glu Arg Gly Ser Leu Arg Glu Val Leu Asn Asp Thr
                565                 570                 575

Ile Ser Tyr Pro Asp Gly Thr Phe Met Asp Trp Glu Phe Lys Ile Ser
                580                 585                 590

Val Leu Tyr Asp Ile Ala Lys Gly Met Ser Tyr Leu His Ser Ser Lys
                595                 600                 605

Thr Glu Val His Gly Arg Leu Lys Ser Thr Asn Cys Val Val Asp Ser
            610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
                645                 650                 655

Ile Ser Gln Lys Gly Asp Val Tyr Ser Tyr Gly Ile Ile Ala Gln Glu
                660                 665                 670

Ile Ile Leu Arg Lys Glu Thr Phe Tyr Thr Leu Ser Cys Arg Asp Arg
            675                 680                 685

Asn Glu Lys Ile Phe Arg Val Glu Asn Ser Asn Gly Met Lys Pro Phe
            690                 695                 700

Arg Pro Asp Leu Phe Leu Glu Thr Ala Glu Glu Lys Glu Leu Glu Val
705                 710                 715                 720

Tyr Leu Leu Val Lys Asn Cys Trp Glu Glu Asp Pro Glu Lys Arg Pro
                725                 730                 735

Asp Phe Lys Lys Ile Glu Thr Thr Leu Ala Lys Ile Phe Gly Leu Phe
                740                 745                 750

His Asp Gln Lys Asn Glu Ser Tyr Met Asp Thr Leu Ile Arg Arg Leu
            755                 760                 765

Gln Leu Tyr Ser Arg Asn Leu Glu His Leu Val Glu Glu Arg Thr Gln
            770                 775                 780

Leu Tyr Lys Ala Glu Arg Asp Arg Ala Asp Arg Leu Asn Phe Met Leu
785                 790                 795                 800

Leu Pro Arg Leu Val Val Lys Ser Leu Lys Glu Lys Gly Phe Val Glu
                805                 810                 815

Pro Glu Leu Tyr Glu Glu Val Thr Ile Tyr Phe Ser Asp Ile Val Gly
                820                 825                 830

Phe Thr Thr Ile Cys Lys Tyr Ser Thr Pro Met Glu Val Val Asp Met
            835                 840                 845

Leu Asn Asp Ile Tyr Lys Ser Phe Asp His Ile Val Asp His His Asp
            850                 855                 860

Val Tyr Lys Val Glu Thr Ile Gly Asp Ala Tyr Met Val Ala Ser Gly
865                 870                 875                 880

Leu Pro Lys Arg Asn Gly Asn Arg His Ala Ile Asp Ile Ala Lys Met
                885                 890                 895

Ala Leu Glu Ile Leu Ser Phe Met Gly Thr Phe Glu Leu Glu His Leu
                900                 905                 910

Pro Gly Leu Pro Ile Trp Ile Arg Ile Gly Val His Ser Gly Pro Cys
            915                 920                 925

Ala Ala Gly Val Val Gly Ile Lys Met Pro Arg Tyr Cys Leu Phe Gly
            930                 935                 940

Asp Thr Val Asn Thr Ala Ser Arg Met Glu Ser Thr Gly Leu Pro Leu
945                 950                 955                 960

Arg Ile His Val Ser Gly Ser Thr Ile Ala Ile Leu Lys Arg Thr Glu
                965                 970                 975
```

-continued

```
Cys Gln Phe Leu Tyr Glu Val Arg Gly Glu Thr Tyr Leu Lys Gly Arg
            980                 985                 990
Gly Asn Glu Thr Thr Tyr Trp Leu Thr Gly Met Lys Asp Gln Lys Phe
        995                 1000                1005
Asn Leu Pro Thr Pro Pro Thr Val Glu Asn Gln Gln Arg Leu Gln Ala
    1010                1015                1020
Glu Phe Ser Asp Met Ile Ala Asn Ser Leu Gln Lys Arg Gln Ala Ala
1025                1030                1035                1040
Gly Ile Arg Ser Gln Lys Pro Arg Val Ala Ser Tyr Lys Lys Gly
            1045                1050                1055
Thr Leu Glu Tyr Leu Gln Leu Asn Thr Thr Asp Lys Glu Ser Thr Tyr
            1060                1065                1070
Phe

<210> SEQ ID NO 3
<211> LENGTH: 22
<212> TYPE: DNA
<213> ORGANISM: Homo sapiens

<400> SEQUENCE: 3
agcaagtggg cacaaggagt at                                           22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
gcgttcacag tcacatttag gc                                           22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
aagtgggcac aaggagtatg gt                                           22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6
gcgttcacag tcacatttag gc                                           22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Novel
      Sequence
```

-continued

```
<400> SEQUENCE: 7
agtgggcaca aggagtatgg tt                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8
gcagtcgcct gagttatgaa tc                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
agtgggcaca aggagtatgg tt                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
gcgttcacag tcacatttag gt                                              22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
tgggcacaag gagtatggtt cta                                             23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12
gcgttcacag tcacatttag gc                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 13
```
gggcacaagg agtatggttc ta                                               22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 14
gcagtcgcct gagttatgaa tc                                               22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 15
gggcacaagg agtatggttc ta                                               22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 16
gtagcgttca cagtcacatt tagg                                             24

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17
ggcacaagga gtatggttct aa                                               22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 18
gaaagtagcg ttcacagtca ca                                               22

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19

```
gtgaatgagg ggctggaaat agt                                            23
```

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 20

```
ggcagtcgcc tgagttatga at                                             22
```

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 21

```
tgaatgaggg gctggaaata gt                                             22
```

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 22

```
ggcagtcgcc tgagttatga at                                             22
```

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 23

```
tgaatgaggg gctggaaata gt                                             22
```

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 24

```
gcagtcgcct gagttatgaa tc                                             22
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 25

```
gaatgagggg ctggaaatag tg                                             22
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 26
cgagttcgtg ggagaaatag ga                                          22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 27
gaatgagggg ctggaaatag tg                                          22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 28
ggcagtcgcc tgagttatga at                                          22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 29
gaatgagggg ctggaaatag tg                                          22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 30
gcagtcgcct gagttatgaa tc                                          22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 31 aatgagggc tggaaatagt ga                                           22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 32
cgagttcgtg ggagaaatag ga                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 33
aatgaggggc tggaaatagt ga                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 34
ggcagtcgcc tgagttatga at                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 35
atgaggggct ggaaatagtg ag                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 36
cgagttcgtg ggagaaatag ga                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 37
atgaggggct ggaaatagtg ag                                              22

```
<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 38
gcagtcgcct gagttatgaa tc                                                    22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 39 gagggctgg aaatagtgag ag                                                     22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 40
gcagtcgcct gagttatgaa tc                                                    22

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 41
gggctggaaa tagtgagagg acg                                                   23

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 42
gcagtcgcct gagttatgaa tc                                                    22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 43
gggctggaaa tagtgagagg ac                                                    22

<210> SEQ ID NO 44
```

```
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 44
cagtcgcctg agttatgaat ca                                            22

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 45
gggctggaaa tagtgagagg acg                                           23

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 46
cgagttcgtg ggagaaatag ga                                            22

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 47
gggctggaaa tagtgagagg acg                                           23

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 48
ggcagtcgcc tgagttatga at                                            22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 49
cggatggtct gattcataac tc                                            22

<210> SEQ ID NO 50
<211> LENGTH: 22
```

```
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 50
gtgggagaaa taggaaacgc ta                                              22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 51
ctggagcact tcgtatgttt ac                                              22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 52
ggtgatagat tcctggagaa ag                                              22

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 53
gtttcctatt tctcccacga actc                                            24

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 54
tttcttggtg tccacagagg ta                                              22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 55
gtttcctatt tctcccacga ac                                              22

<210> SEQ ID NO 56
<211> LENGTH: 22
<212> TYPE: DNA
```

<213> ORGANISM: Artificial Sequence
<220> FEATURE:
<223> OTHER INFORMATION: Description of Artificial Sequence: Novel
      Sequence

<400> SEQUENCE: 56
cgtcataccc ttcaaaagtg ag                                              22

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 57
gtttcctatt tctcccacga actc                                            24

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 58
gaactctgga ccaccacaca taa                                             23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 59
ggaccacaac aggaaaagca atg                                             23

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 60
aggcaagagc aaagtctcgt tt                                              22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 61
ggaccacaac aggaaaagca at                                              22

<210> SEQ ID NO 62
<211> LENGTH: 22
<212> TYPE: DNA
<213> ORGANISM: Artificial Sequence

```
<220> FEATURE:
<223> OTHER INFORMATION: Description of Artificial Sequence: Novel
      Sequence

<400> SEQUENCE: 62
cagcgtcaga acaaggacat tt                                                 22

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 63
gactataaag aaaccttaac caggc                                              25

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 64
ggaccaccac acataataat cac                                                23

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 65
ccttgacaca gaattgagct ac                                                 22

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 66
ggaccaccac acataataat cac                                                23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 67
aatgaggggc tggaaatagt gag                                                23

<210> SEQ ID NO 68
<211> LENGTH: 22
<212> TYPE: DNA
<213> ORGANISM: Artificial Sequence
<220> FEATURE:
```

<223> OTHER INFORMATION: Description of Artificial Sequence: Novel
      Sequence

<400> SEQUENCE: 68
gcagtcgcct gagttatgaa tc                                               22

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 69
gtcctggatc ccccaggtga gtcagaactg cc                                    32

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 70
ggccgaattc ggtgctactc cggcagtcgc c                                     31

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 71
tcatggatcc ggcgactgcc ggagtagcac c                                     31

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 72
ggaattccca ggagacagcg                                                  20

<210> SEQ ID NO 73
<211> LENGTH: 63
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 73
attgcagtct tcaccctcac tggagctgtg gtgctgctcc tgctcgtcgc tctcctgatg       60
ctc                                                                    63

<210> SEQ ID NO 74
<211> LENGTH: 60
<212> TYPE: DNA
<213> ORGANISM: Artificial Sequence -continued
<220> FEATURE:
<223> OTHER INFORMATION: Description of Artificial Sequence: Novel
      Sequence

<400> SEQUENCE: 74
taacgtcaga agtgggagtg acctcgacac gacgaggacg agcagcgaga ggactacgag     60

METHODS OF AND KITS AND COMPOSITIONS FOR DIAGNOSING COLORECTAL TUMORS AND METASTASIS THEREOF

CROSS-REFERENCE TO RELATED APPLIATIONS

This application is the National Phase of International patent application Ser. No. PCT/US97/07467, filed May 2, 1997, and claims benefit of provisional application Ser. No. 60/016,564, filed May 3, 1996.

FIELD OF THE INVENTION

The present invention relates to compositions and kits for and methods of detecting metastasized colorectal tumor cells in samples. The present invention also relates to compositions and kits for and methods of evaluating the extent of invasive activity of colorectal tumor cells in samples from the colon.

BACKGROUND OF THE INVENTION

Colorectal cancer is the third most common neoplasm worldwide and the second most common in the United States, representing about 15% of the newly diagnosed cases of cancer in the United States. The large intestine or large bowel is the third leading site for the development of new cancer and is diagnosed in about 150,000 patients each year. Colorectal cancer is the second leading cause of cancer-related deaths and is responsible for about 12% of cancer deaths in the United States. The mortality rate of newly diagnosed large bowel cancer approaches 50% and there has been little improvement over the past 40 years. Most of this mortality reflects local, regional and distant metastases. About thirty percent of patients with colorectal cancer have unresectable disease at presentation and about 40% develop metastases during the course of their disease. Distant metastatic disease is seen in liver (about 12%), lung (about 3%), bone (about 0.9%), brain (about 0.7%), nodes (about 4%), and peritoneum (about 2%) at the time of initial diagnosis. In 1987, the large bowel cancers found regionally or at distant sites at the time of diagnosis were about 26i and about 18%, respectively.

Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recrudescence. Overall recurrence rates for colonic tumors are about 33% and for rectal cancer about 42%. Of these recurrences, about 9% are local, about 13% are systemic metastatic disease, and the remaining 88% are a combination of local and systemic disease. Fifty percent of patients with recurrent colorectal cancer have hepatic metastases.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. The 5 year relative survival rates for patients with regional or distant metastases are 48% and 5%, compared with 90% and 77% for disease which is in situ or local, respectively, at the time of diagnosis. Similarly, diagnosis of metastatic or recurrent disease earlier potentially carries with it a better prognosis.

Immunoscintigraphy using monoclonal antibodies directed at tumor-specific markers has been employed to diagnose colorectal cancer. Monoclonal antibodies against carcinoembryonic antigen (CEA) labeled with $^{99}$Technetium identified 94% of patients with recurrent tumors. Similarly, $^{111}$Indium-labeled anti-CEA monoclonal antibodies successfully diagnosed 85% of patients with recurrent colorectal carcinoma who were not diagnosed by conventional techniques. $^{125}$Iodine-labeled antibodies have been effective in localizing more than 80% of the pathologically-confirmed recurrences by intraoperative gamma probe scanning.

There remains a need for compositions and kits which can specifically detect metastasized colorectal cancer cells using samples removed from or discharged by an individual being screened for, suspected of suffering from or suspected of being susceptible to metastasized colorectal tumors. There remains a need for methods of identifying individuals suffering from metastasized colorectal tumors using samples removed from or discharged by an individual being screened for, suspected of suffering from or suspected of being susceptible to metastasized colorectal tumors.

SUMMARY OF THE INVENTION

The present invention relates to in vitro methods of determining whether or not an individual has metastasized colorectal cancer cells. The present invention relates to in vitro methods of examining samples of extraintestinal tissue and body fluids from an individual to determine whether or not ST receptor protein, which is a protein that is specific to colorectal cells including colorectal tumor cells, is being expressed extraintestinally. The presence of specific sequences of the ST receptor protein or of nucleic acid molecules that encode specific sequences of ST receptor protein and that are indicative of expression of the ST receptor protein is evidence that the individual is suffering from metastasized colorectal cancer. According to the present invention, methods and compositions are provided for detecting either 1) the extracellular portion of the ST receptor protein (amino acids 24–430 of SEQ ID NO:2), 2) the 63 carboxy terminal amino acid sequence of the ST receptor protein (amino acids 1031–1093 of SEQ ID NO:2), 3) the mRNA sequence that encodes the extracellular portion of the ST receptor protein (amino acids 24–430 which are encoded by nucleotides 72–1290 of SEQ ID NO:1), or 4) the mRNA sequence that the 63 carboxy terminal amino acid sequence of the ST receptor protein (amino acids 1031–1093 which are encoded by nucleotides 3091–3274 of SEQ ID NO:1).

The present invention relates to in vitro methods of determining whether or not tumor cells are colorectal in origin. The present invention relates to in vitro methods of diagnosing whether or not an individual suffering from cancer is suffering from colorectal cancer. The present invention relates to in vitro methods of examining samples of tumors from an individual to determine whether or not ST receptor protein, which is a protein that is specific to colorectal cells including colorectal tumor cells, is being expressed by the tumor cells. The presence of the ST receptor protein or of nucleic acid molecules that are indicative of expression of the ST receptor protein is evidence that the individual is suffering from colorectal cancer. The presence of the ST receptor protein or mRNA encoding the ST receptor is determined by identifying the presence of either 1) the extracellular portion of the ST receptor protein (amino acids 24–430), 2) the 63 carboxy terminal amino acid sequence of the ST receptor protein (amino acids 1031–1093), 3) the mRNA sequence that encodes the extracellular portion of the ST receptor protein (amino acids 24–430 encoded by nucleotides 72–1290), or 4) the mRNA sequence that the 63 carboxy terminal amino acid sequence of the ST receptor protein (amino acids 1031–1093 encoded by nucleotides 3091–3274).

The present invention relates to in vitro kits for practicing the methods of the invention and to reagents and compositions useful to practice the methods, for example as components in such in vitro kits of the invention. According to the present invention, in vitro kits and reagents are provided for practicing methods detecting, in a sample, the presence of either 1) the extracellular portion of the ST receptor protein (amino acids 24–430), 2) the 63 carboxy terminal amino acid sequence of the ST receptor protein (amino acids 1031–1093), 3) the mRNA sequence that encodes the extracellular portion of the ST receptor protein (amino acids 24–430 encoded by nucleotides 72–1290), or 4) the mRNA sequence that the 63 carboxy terminal amino acid sequence (amino acids 1031–1093 encoded by nucleotides 3091–3274) of the ST receptor protein.

In some embodiments of the invention, extraintestinal tissue and fluid samples, i.e. non-colorectal tissue and fluid samples, may be screened to identify the presence or absence of the ST receptor protein. Techniques such as an ST receptor/ligand binding assays, ELISA assays and. Western blots may be performed to determine whether the ST receptor is present in a sample. According to the present invention, the presence or absence of either the extracellular portion of the ST receptor protein (amino acids 24–430), or the 63 carboxy terminal amino acid sequence of the ST receptor protein may be detected (amino acids 1031–1093).

In some embodiments of the invention, extraintestinal tissue and fluid samples, i.e. non-colorectal tissue and fluid samples, may be screened to identify whether ST receptor protein is being expressed in extraintestinal cells by detecting the presence or absence of mRNA that encodes the ST receptor protein. The presence of mRNA that encodes the ST receptor protein or cDNA generated therefrom can be determined using techniques such as PCR amplification including RT-PCR amplification, Northern Blots (mRNA), Southern Blots (cDNA), oligonucleotide hybridization ribonuclease protection assay (RPA), in situ PCR or hybridization, S1-nuclease protection assay, immune-capture RT-PCR, nucleic acid sequence-based amplification (NASBA), branched DNA (bDNA) technology, and strand-displacement amplification (SDA). According to the present invention, the presence or absence of either the mRNA sequence that encodes the extracellular portion of the ST receptor protein (amino acids 24–430 encoded by nucleotides 72–1290), or the mRNA sequence that the 63 carboxy terminal amino acid sequence of the ST receptor protein may be detected (amino acids 1031–1093 encoded by nucleotides 3091–3274).

In some embodiments of the invention, cells of extraintestinal tissue samples, i.e. non-colorectal tissue samples, may be examined to identify the presence or absence of the ST receptor protein. Techniques such as an ST receptor/ligand binding or immunohistochemistry blots may be performed on tissue sections to determine whether the ST receptor is present in a sample. According to the present invention, the presence or absence of either the extracellular portion of the ST receptor protein (amino acids 24–430), or the 63 carboxy terminal amino acid sequence of the ST receptor protein (amino acids 1031–1093) may be detected.

In some embodiments of the invention, cells of extraintestinal tissue samples, i.e. non-colorectal tissue samples, may be examined to determine whether ST receptor protein is being expressed in extraintestinal cells by detecting the presence or absence of mRNA that encodes the ST receptor protein. The presence of mRNA that encodes the ST receptor protein or cDNA generated therefrom in cells from tissue sections can be determined using techniques such as in situ hybridization. According to the present invention, the presence or absence of either the mRNA sequence that encodes the extracellular portion of the ST receptor protein (amino acids 24–430 encoded by nucleotides 72–1290), or the mRNA sequence that the 63 carboxy terminal amino acid sequence of the ST receptor protein (amino acids 1031–1093 encoded by nucleotides 3091–3274) may be detected.

Another aspect of the invention relates to methods of analyzing tissue samples from the colon tissue to evaluate the extent of metastasis or invasion of colorectal tumor cells into the laminapropria. The laminapropria represents the barrier between the colorectal tract and the rest of the body; see *Bailey's Textbook of Histology*, 16th edition, Coperhaven et al. 1975 Williams and Wilkens, Baltimore Md. at page 404 which is incorporated herein by reference. By identifying the presence of ST receptor or mRNA that encodes ST receptor protein in cells of the laminapropria, the extent of invasion/infiltration of colorectal tumor cells into extraintestinal tissue can be evaluated and confirmed. According to the present invention, the presence or absence of either 1) the extracellular portion of the ST receptor protein (amino acids 24–430), 2) the 63 carboxy terminal amino acid sequence of the ST receptor protein (amino acids 1031–1093), 3) the mRNA sequence that encodes the extracellular portion of the ST receptor protein (amino acids 24–430 encoded by nucleotides 72–1290), or 4) the mRNA sequence that the 63 carboxy terminal amino acid sequence of the ST receptor protein (amino acids 1031–1093 encoded by nucleotides 3091–3274) may be detected in cells of the laminapropria.

The present invention relates to in vitro kits fdr evaluating tissues samples to determine the level of metastasis and to reagents and compositions useful to practice the same. In some embodiments of the invention, tissue samples which include sections of the laminapropria may be isolated from individuals undergoing or recovering from surgery to remove colorectal tumors. The tissue is analyzed to determine the extent of invasion into the basement membrane of the laminapropria by neoplastic colorectal cells. Identification of the presence or absence of the ST receptor protein confirms evaluation of the migration of tumor cells into the basement membrane indicating metastasis. Techniques such as an ST receptor/ligand binding and immunohistochemistry assays may be performed to determine whether the ST receptor is present in cells in the tissue sample which are indicative of metastatic migration. Alternatively, in some embodiments of the invention, tissue samples that include the laminapropria are analyzed to identify whether ST receptor protein is being expressed in cells in the tissue sample which indicates metastatic migration by detecting the presence or absence of mRNA that encodes the ST receptor protein. The presence of mRNA that encodes the ST receptor protein or cDNA generated therefrom can be determined using techniques such as in situ hybridization. According to the present invention, the presence or absence of either 1) the extracellular portion of the ST receptor protein (amino acids 24–430), 2) the 63 carboxy terminal amino acid sequence of the ST receptor protein (amino acids 1031–1093), 3) the mRNA sequence that encodes the extracellular portion of the ST receptor protein (amino acids 24–430 encoded by nucleotides 72–1290), or 4) the mRNA sequence that the 63 carboxy terminal amino acid sequence of the ST receptor protein (amino acids 1031–1093 encoded by nucleotides 3091–3274), may be detected in cells of tissue to determine the extent of invasion into the basement membrane of the laminapropria by neoplastic colorectal cells.

DESCRIPTION OF PREFERRED EMBODIMENTS OF THE INVENTION

As used herein, the terms "ST" and "native ST" are used interchangeably and are meant to refer to heat-stable toxin (ST) which is a peptide produced by E. coli, as well as other organisms. STs are naturally occurring peptides which 1) are naturally produced by organisms, 2) which bind to the ST receptor and 3) which activate the signal cascade that mediates ST-induced diarrhea.

As used herein, the term "ST receptor" is meant to refer to the receptors found on colorectal cells, including local and metastasized colorectal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum. The nucleotide sequence that encodes human ST receptor protein has been cloned and the amino acid and nucleotide sequences are described in F. J. Sauvage et al. 1991 *J. Biol. Chem.* 266:17912–17918, each of which is incorporated herein by reference.

As used herein, the term "extracellular portion of the ST receptor" is meant to refer to, from N terminal to C terminal, amino acids 24–430 of the ST receptor protein.

As used herein, amino acids 24–430 is meant to refer to amino acids 24–430 of SEQ ID NO:2 or the corresponding sequences from an allelic variant of ST receptor protein.

As used herein, nucleotides 72–1290 is meant to refer to nucleotides 72–1290 of SEQ ID NO:1 or the corresponding sequences from an allelic variant of ST receptor protein.

As used herein, the term "carboxy tail of the ST receptor" is meant to refer to, from N terminal to C terminal, the 63 most C terminal amino acids of the ST receptor protein, i.e. amino acids 1031–1093 of the ST receptor protein.

As used herein, amino acids 1031–1093 is meant to refer to amino acids 1031–1093 of SEQ ID NO:2 or the corresponding sequences from an allelic variant of ST receptor protein.

As used herein, nucleotides 3091–3274 is meant to refer to nucleotides 3091–3274 of SEQ ID NO:1 or the corresponding sequences from an allelic variant of ST receptor protein.

As used herein, the term "ST receptor ligand" is meant to refer to compounds which specifically bind to the ST receptor. ST is an ST receptor ligand. An ST receptor ligand may be a peptide or a non-peptide. ST receptor ligands are described in U.S. patent application Ser. No. 08/141,892, filed Oct. 26, 1993, which is incorporated herein by reference.

As used herein, the term "ST receptor binding peptide" is meant to refer to ST receptor ligands that are peptides.

As used herein, the term "ST peptides" is meant to refer to ST receptor binding peptides described in U.S. patent application Ser. No. 08/141,892, filed Oct. 26, 1993 which is incorporated herein by reference, U.S. patent application Ser. No. 08/305,056 filed Sep. 13, 1994 which is incorporated herein by reference, and PCT Application Serial No. PCT/US94/12232 filed Oct. 26, 1994 and published as International Publication Serial No. WO 95/11694 with International Publication Date May 4, 1996, which is incorporated herein by reference.

As used herein, the term "fragment" is meant to refer to peptide a) which has an amino acid sequence identical to a portion of an ST receptor binding peptide and b) which is capable of binding to the ST receptor.

As used herein, the term "derivative" is meant to refer to a peptide a) which has an amino acid sequence substantially identical to at least a portion of an ST receptor binding peptide and b) which is capable of binding to the ST receptor.

As used herein, the term "substantially identical" is meant to refer to an amino acid sequence that is the same as the amino acid sequence of an ST peptide except some of the residues are deleted or substituted with conservative amino acids or additional amino acids are inserted.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain ST receptors and are therefore amenable to the methods of the present invention using the compounds of the present invention.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to metastasized colorectal cancer cells.

As used herein, the term "metastasized colorectal cancer cells" is meant to refer to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, the term "non-colorectal sample" and "extra-intestinal sample" are used interchangeably and meant to refer to a sample of tissue or body fluid from a source other than colorectal tissue. In some preferred embodiments, the extraintestinal sample is a sample of tissue such as lymph nodes. In some preferred embodiments, the non-colorectal sample is a sample of extra-intestinal tissue which is an adenocarcinoma of unconfirmed origin. In some preferred embodiments, the extraintestinal sample is a blood sample.

As used herein, "an individual suffering from an adenocarcinoma of unconfirmed origin" is meant to refer to an individual who has a tumor in which the origin has not been definitively identified.

As used herein, "an individual is suspected of being susceptible to metastasized colorectal cancer" is meant to refer to an individual who is at a particular risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence.

Advancements in the understanding of genetics and developments in technology as well as epidemiology allow for the determination of probability and risk assessment an individual has for developing colorectal cancer. Using family health histories and/or genetic screening, it is possible to estimate the probability that a particular individual has for developing certain types of cancer including colorectal cancer. Those individuals that have been identified as being predisposed to developing a particular form of cancer can be monitored or screened to detect evidence of metastasized colorectal cancer. Upon discovery of such evidence, early treatment can be undertaken to combat the disease.

Similarly, those individuals who have already developed colorectal cancer and who have been treated to remove the cancer or are otherwise in remission are particularly susceptible to relapse and reoccurrence including the metastasis of tumors. Such individuals can be monitored and screened to detect evidence of metastasis and upon discovery of such evidence, early treatment can be undertaken to combat the disease.

ST, which is produced by *E. coli*, as well as other organisms, is responsible for endemic diarrhea in developing countries and travelers diarrhea. ST induces intestinal secretion by binding to specific receptors, ST receptors, in the apical brush border membranes of the mucosal cells lining the intestinal tract. Binding of ST to ST receptors is non-covalent and occurs in a concentration-dependent and saturable fashion. Once bound, ST-ST receptor complexes appear to be internalized by intestinal cells, i.e. transported from the surface into the interior of the cell. Binding of ST to ST receptors triggers a cascade of biochemical reactions in the apical membrane of these cells resulting in the production of a signal which induces intestinal cells to secrete fluids and electrolytes, resulting in diarrhea.

ST receptors are unique in that they are only localized in the apical brush border membranes of the cells lining the intestinal tract. Indeed, they are not found in any other cell type in placental mammals. In addition, ST receptors are almost exclusively localized to the apical membranes, with little being found in the basolateral membranes on the sides of intestinal cells.

Mucosal cells lining the intestine are joined together by tight junctions which form a barrier against the passage of intestinal contents into the blood stream and components of the blood stream into the intestinal lumen.

In individuals suffering from colorectal cancer, the cancer cells are often derived from cells that produce and display the ST receptor and these cancer cells continue to produce and display the ST receptor on their cell surfaces. Indeed, T84 cells, which are human colonic adenocarcinoma cells isolated from lung metastases, express ST receptors on their cell surface. Similarly, HT29glu-cells, which are human colonic adenocarcinoma cells, express receptors for ST. Thus, in individuals suffering from colorectal cancer, some metastasized intestinal cancer cells express ST receptors;

An effort was undertaken to determine tae proportion of colorectal tumors which have the ST receptor. Each of the tumors tested were independently confirmed to be colorectal cancer by standard techniques of surgical pathology. Every one of the colorectal cancer tumors tested, includingff focal colorectal tumors and metastasized tumors (liver, lung, lymph node, peritoneum, gall bladder), possessed ST receptors. In each case, the affinity and density of receptors was amenable for targeting. That is, the cells possessed at least $10^4$–$10^6$ receptors per cell and demonstrated an affinity of $10^{-7}$ or better (that is preferably between $18^{-8}$ to $10^{-9}$ or less; the lower number indicating a tighter bond, thus a higher affinity). Normal liver, lymph node, peritoneum and lung cells were found not to possess ST receptors.

When such cancer cells metastasize, the metastasized cancer cells continue to produce and display the ST receptor. The expression of ST receptors on the surfaces of metastatic tumors provides a target for selective binding of conjugated compositions. ST receptors permit the absolutely specific targeting of diagnostic agents to metastatic colorectal cancer cells.

ST receptor protein and mRNA encoding ST receptor protein permit the absolutely specific targeting of diagnostic agents to metastatic colorectal cancer cells.

According to the present invention, specific portions of ST receptor protein and specific mRNA sequences that encode specific portions of the ST receptor protein provide the means to more specifically and accurately target metastatic colorectal cancer cells using diagnostic tools. These portions refer specifically to the extracellular membrane portion of the ST receptor protein and the tail of the ST receptor protein.

In some embodiments, diagnostic methods and kits of the present invention are specifically targeted to detecting metastatic disease. In other embodiments, methods and kits are provided for evaluating whether or not a tumor is colorectal in origin. In other embodiments, methods and kits are provided for evaluating the metastatic migration of tumor cells in the laminapropria, indicating the level of invasion of colorectal tumor cells into the basement membrane.

According to the invention, compounds are provided which bind to ST receptor protein or mRNA encoding the receptor. Normal tissue in the body does not have ST receptors or mRNA encoding ST receptors except cells of the intestinal tract. Thus, if extraintesinal samples possess ST receptors metastasis of colorectal tumor cells is indicated. Thus, metastasized colorectal cells may be identified by detecting in extraintestinal samples ST receptors or mRNA encoding ST receptors. The expression of ST receptor is a marker for cell type and allows for the identification of colorectal metastasis in extra-intestinal samples. Moreover, expression of ST receptor is a marker for cell type and allows for the identification of the origin of adenocarcinoma of unconfirmed origin as colorectal tumors. Additionally, expression of ST receptor is useful to visualize and confirm the invasion of colorectal neoplasms into the basement membrane of the laminapropria.

Patients

Patients With Adenocarcinomas:

The invention can be used to identify colorectal tumors in samples of tumors removed from individuals suffering from adenocarcinomas of unconfirmed origin. Screening/monitoring Patients:

Individuals who are at risk for developing metastasized colorectal cancer may be screened using the in vitro diagnostic methods of the present invention. The invention is particularly useful for monitoring individuals whose family medical history includes relatives who have suffered from colorectal cancer. Likewise, the invention is useful to monitor individuals who have been diagnosed as having colorectal cancer and, particularly those who have been treated and had tumors removed and/or are otherwise experiencing remission.

Surgical Patients to be Evaluated:

For aspects of the invention related to analysis of lumen tissue, the invention is useful to evaluate the level of metastatic migration of colorectal tumor cells using lumen samples taken from surgery patients at and near the site of the tumor.

Samples

Tissue Samples:

Non-colorectal tissue samples may be obtained from any extraintestinal tissue, i.e. tissue from sites other than those in the intestinal tract below the small intestine (i.e. the large intestine (colon), including the cecum, ascending colon, transverse colon, descending colon, and sigmoid colon, and rectum) and additionally the duodenum and small intestine (jejunum and ileum). The cells of all tissues except those of that are intestinal do not express the ST receptor. Thus if the ST receptor protein or mRNA encoding the ST receptor protein are detected in extraintesinal samples, the presence of metastatic colorectal cancer cells is indicated. In some preferred embodiments, the tissue samples are lymph nodes.

Tissue samples may be obtained by standard surgical techniques including use of biopsy needles. One skilled in the art would readily appreciate the variety of test samples that may be examined for ST receptor protein and recognize methods of obtaining tissue samples.

Tissue samples may be homogenized or otherwise prepared for screening for the presence of ST receptor protein by well known techniques such as sonication, mechanical disruption, chemical lysis such as detergent lysis or combinations thereof.

Tumor Samples:

Samples from tumors may be identified as colorectal in origin by identification of expression of ST receptors using the methods of the invention. Samples of tumors removed from individuals suffering from adenocarcinomas of unconfirmed origin can be tested to determine whether or not they possess ST receptor protein or mRNA encoding ST receptor protein. If the sample is removed from the intestinal track, a section of frozen cells can be examined to determine if the tumor cells express ST receptor protein. If the sample is removed from the extra-intestinal tissue, a section of frozen cells can be examined to determine if the tumor cells express ST receptor protein or the sample can be homogenized and tested since the non-cancer cells will not possess ST receptors and therefore not present background.

Samples may be obtained from resected tissue or biopsy material including needle biopsy. Tissue section preparation for surgical pathology may be frozen and prepared using standard techniques. In ST binding assays on tissue sections, ST is added before fixing cells. Immunohistochemistry and in situ hybridization binding assays on tissue sections are performed in fixed cells. Extra-intestinal samples may be homogenized by standard techniques such as sonication, mechanical disruption or chemical lysis such as detergent lysis. It is also contemplated that tumor samples in body fluids, excretions and/or secretion such as blood, urine, lymph fluid, cerebral spinal fluid, amniotic fluid, vaginal fluid, semen and stool samples may also be screened to determine if such tumors are colorectal in origin.

Body Fluid Samples:

Examples of body fluid samples include blood, urine, lymph fluid, cerebral spinal fluid, amniotic fluid, vaginal fluid and semen. In some preferred embodiments, blood is used as a sample of body fluid. Cells may be isolated from fluid sample such as centrifugation. One skilled in the art would readily appreciate the variety of test samples that may be examined for ST receptor protein. Test samples may be obtained by such methods as withdrawing fluid with a syringe or by a swab. One skilled in the art would readily recognize other methods of obtaining test samples.

In an assay using a blood sample, the blood plasma may be separated from the blood cells. The blood plasma may be screened for ST receptor protein including truncated protein which is released into the blood when the ST receptor protein is cleaved from or sloughed off from metastasized colorectal tumor cells. In some embodiments, blood cell fractions are screened for the presence of metastasized colorectal tumor cells. In some embodiments, lymphocytes present in the blood cell fraction are screened by lysing the cells and detecting the presence of ST receptor protein or mRNA encoding ST receptor protein which may be present as a result of the presence of any metastasized colorectal tumor cells that may have been engulfed by the blood cell.

Laminapropria Tissue Samples:

Samples of the laminapropria are removed during colorectal tumor removal surgery such as by resection or colonoscopy. The sample including basement membrane cells is frozen. If an ST binding assay is to be performed, the labelled ST is contacted to the frozen section and the cells are then fixed and stained. If immunohistochemistry or in situ hybridization is to be performed, the frozen section is stained and then the assay is run. Those having ordinary skill in the art can readily isolate samples which include portions of the laminapropria and fix and stain them using standard techniques. By adding the visualization provided with an ST receptor detection technique, the section can be more comprehensively analyzed and the level of invasion of neoplastic colorectal cells into the laminapropria can be determined. The present invention may be used to analyze and evaluate the extent of progression of localized colorectal tumors, that is primary or non-metastatic colorectal tumors, if these have penetrated the basement membrane underlying the mucosa into the submucosa.

Assays

Immunoassay:

The present invention relates to immunoassay methods of identifying individuals suffering from colorectal cancer metastasis by detecting presence of ST receptor protein in samples of extraintestinal tissue or body fluids using antibodies which were produced in response to exposure to ST receptor protein.

The present invention also relates to immunoassay methods of identifying individuals suffering from colorectal cancer by detecting the presence of ST receptor protein in samples of tumor using antibodies which were produced in response to exposure to ST receptor protein.

The antibodies are preferably monoclonal antibodies. The antibodies are preferably raised against ST receptor protein made in human cells. Immunoassays are well known and their design may be routinely undertaken by those having ordinary skill in the art. Those having ordinary skill in the art can produce monoclonal antibodies which specifically bind to ST receptor protein and are useful in methods and kits of the invention using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, and which provides detailed guidance for the production of hybridomas and monoclonal antibodies which specifically bind to target proteins. It is within the scope of the present invention to include FAbs and F(Ab)2s which specifically bind to ST receptor in place of antibodies.

Briefly, the ST receptor protein is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the ST receptor protein, the hybridoma which produces them is cultured to produce a continuous supply of anti-ST receptor protein-specific antibodies.

The present invention relates to antibodies which are produced in response to exposure to ST receptor protein. The antibodies are preferably monoclonal antibodies. The antibodies are preferably raised against ST receptor protein made in human cells. In some embodiments, antibodies specifically bind to the extracellular domain of ST receptor protein. In some embodiments, antibodies specifically bind to the transmembrane domain. In some embodiments, antibodies specifically bind to the cytoplasmic domain. The antibodies preferably bind to the extracellular domain of ST receptor protein. In particular, the antibodies preferably bind to amino acids 24–430 of ST receptor protein. In some embodiments, the antibodies bind to the C-terminal tail of ST receptor protein, i.e. amino acids 1031–1093.

The means to detect the presence of a protein in a test sample are routine and one having ordinary skill in the art can detect the presence or absence of a protein or an antibody using well known methods. One well known method of detecting the presence of a protein is an immunoassay. One having ordinary skill in the art can readily appreciate the multitude of ways to practice an immunoassay to detect the presence of ST receptor protein in a sample.

According to some embodiments, immunoassays comprise allowing proteins in the sample to bind a solid phase support such as a plastic surface. Detectable antibodies, preferably those which bind to the extracellular domain (amino acids 24–430) are then added which selectively binding to the ST receptor protein. Detection of the detectable antibody indicates the presence of ST receptor protein. The detectable antibody may be a labeled or an unlabelled antibody. Unlabelled antibody may be detected using a second, labelled antibody that specifically binds to the first antibody or a second, unlabelled antibody which can be detected using labelled protein A, a protein that complexes with antibodies. Various immunoassay procedures are described in *Immunoassays for the 80's*, A. Voller et al., Eds., University Park, 1981, which is incorporated herein by reference.

Simple immunoassays may be performed in which a solid hase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable.

After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method, Kirkham*, Ed., E. & S. Livingstone, Edinburgh, 1970, pp. 199–206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of ST receptor in a test sample is anti-ST receptor antibody. By "solid phase support" or "support" is intended any material capable of binding proteins. Well-known solid phase supports include glass, polystyrene, polypropylene, polyethylene, dextran, nylon, amyloses, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of ST receptor protein, detectable anti-ST receptor antibodies are used. Several methods are well known for the detection of antibodies.

One method in which the antibodies can be detectably labeled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labeled is through radioactive isotopes and subsequent use in a radioimmunoassay (RIA) (see, for example, Work, T. S. et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^{3}H$, $^{125}I$, $^{131}I$, $^{35}S$, and $^{14}C$. Preferably $^{125}I$ is the isotope. One skilled in the art would readily recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labeled using fluorescence-emitting metals such as $^{152}Eu$, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibody can also be detectably labeled by coupling to a chemiluminescent compound. The presence of the chemiluminescent-labeled antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colormetric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of ST receptor protein and no ST receptor protein, respectively, are added to assays being performed in parallel with the test assay. One skilled in the art would have the necessary knowledge to perform the appropriate controls.

ST receptor protein may be produced as a reagent for positive controls routinely. One skilled in the art would appreciate the different manners in which the ST receptor protein may be produced and isolated.

An "antibody composition" refers to the antibody or antibodies required for the detection of the protein. For example, the antibody composition used for the detection of ST receptor in a test sample comprises a first antibody that binds ST receptor protein, preferably at the extracellular domain (amino acids 24–430) as well as a second or third detectable antibody that binds the first or second antibody, respectively.

To examine a test sample for the presence of ST receptor protein, a standard immunometric assay such as the one described below may be performed. A first anti-ST receptor protein antibody, which recognizes a specific portion of ST receptor such as the extracellular or cytoplasmic portion, is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from nonspecifically binding the microtiter plate. Test sample are subsequently added to the wells and the plate is incubated for a period of time sufficient for binding to occur. The wells are washed with PBS to remove unbound protein. Labeled anti-ST receptor antibodies, which recognize portions of ST receptor not recognized by the first antibody, are added to the wells. The plate is incubated for a period of time sufficient for binding to occur and subsequently washed with PBS to remove unbound, labeled anti-ST receptor antibody. The amount of labeled and bound anti-ST receptor antibody is subsequently determined by standard techniques.

Kits which are useful for the detection of ST receptor in a test sample comprise a container comprising anti-ST receptor antibodies, in particular those which bind to the extracellular domain (amino acids 24–430) and a container or containers comprising controls. Controls include one control sample which does not contain ST receptor protein and/or another control sample which contains ST receptor protein. The anti-ST receptor antibodies used in the kit are detectable such as being detectably labelled. If the detectable anti-ST antibody is not labelled, it may be detected by second antibodies or protein A for example which may also be provided in some kits in separate containers. Additional components in some kits include solid support, buffer, and instructions for carrying out the assay.

The immunoassay is useful for detecting ST receptor in homogenized tissue samples and body fluid samples including the plasma portion or cells in the fluid sample.

Western Blots:

The present invention relates to methods of identifying individuals suffering from colorectal cancer metastasis by detecting the presence of ST receptor protein in sample of extraintestinal tissue or body fluid using Western blots. Western blots use detectable anti-ST receptor antibodies, preferably those which bind to the extracellular domain (amino acids 24–430) or C terminal tail (amino acids 1031–1093) to bind to any ST,receptor present in a samples and thus indicate the presence of the receptor in the sample.

The present invention also relates to methods of identifying individuals suffering from colorectal cancer using Western blots to detect the presence of ST receptor protein in samples of tumor using antibodies which were produced in response to exposure to ST receptor protein.

Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-ST receptor antibodies described above are useful in Western blot methods. The antibodies preferably bind to the extracellular domain of ST receptor protein. In particular, the antibodies preferably bind to amino acids 24–430 of ST receptor protein. In some embodiments, the antibodies bind to the C-terminal tail of ST receptor protein, i.e. amino acids 1031–1093.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, NY.

Kits which are useful for the detection of ST receptor in a test sample by Western Blot comprise a container comprising anti-ST receptor antibodies, preferably those which bind to the extracellular domain (amino acids 24–430) or C terminal tail (amino acids 1031–1093), and a container or containers comprising controls. Controls include one control sample which does not contain ST receptor protein and/or another control sample which contains ST receptor protein. The anti-ST receptor antibodies used in the kit are detectable such as being detectably labelled. If the detectable anti-ST antibody is not labelled, it may be detected by second antibodies or protein A for example which may also be provided in some kits in separate containers. Additional components in some kits include instructions for carrying out the assay.

Western blots are useful for detecting ST receptor in homogenized tissue samples and body fluid samples including the plasma portion or cells in the fluid sample. ST Binding Assay:

The present invention relates to methods of identifying individuals suffering from colorectal cancer metastasis by detecting presence of ST receptor protein in sample of extraintestinal tissue or body fluid using an ST receptor binding assay. The ST receptor binding assay uses a detectable ST receptor ligand to bind to any ST receptor present and thus indicate the presence of the receptor in a sample.

The present invention also relates to methods of identifying individuals suffering from colorectal cancer by detecting the presence of ST receptor protein in samples of tumor.

In some embodiments, the ST receptor ligand may be native ST. Native ST isolated from *E. coli* is 18 or 19 amino acids in length. The smallest "fragment" of ST which retains activity is the 13 amino acid core peptide extending toward the carboxy terminal from cysteine 6 to cysteine 18 (of the 19 amino acid form). Analogues of ST have been generated by cloning and by chemical techniques. Small peptide fragments of the native ST structure which include the structural determinant that confers binding activity may be constructed. Once a structure is identified which binds to ST receptors, non-peptide analogues mimicking that structure in space are designed. U.S. patent application Ser. No. 08/141, 892, filed Oct. 26, 1993, which is incorporated herein by reference, describes the amino acid sequences of such compounds including derivatives thereof having substantially identical amino acid sequences of ST peptides with deletions and/or insertions and/or conservative substitutions of amino acids and/or comprising D amino acids.

The ST receptor binding assay can be readily performed by those having ordinary skill in the art using readily available starting materials. ST receptor binding assays may be performed a variety of ways but each essentially identify whether or not an ST receptor protein is present in a sample by determining whether or not a detectable ST receptor ligand binds to a receptor in a sample. Briefly, the assay consists of incubating a sample with a constant concentration of an ST ligand such as $1\times10^{-10}$ M to $5\times10^{-10}$ M of $^{125}$I-ST. As a control, a duplicate preparation of a sample known to contain ST receptors are incubated with a duplicate concentration of $^{125}$I-ST. Assays are incubated to equilibrium (for example 2 hours) and the sample is analyzed to determine whether or not $^{125}$I-ST is bound to material in the sample. The $^{125}$I-ST/sample is passed through a filter which is capable of allowing $^{125}$I-ST to pass through but not capable of allowing ST receptor to pass through. Thus, if ST receptor is present in the sample, it will bind the $^{125}$I-ST which will then be trapped by the filter. Detection of $^{125}$I-ST in the filter indicates the presence of ST receptor in the sample. In some preferred embodiments, the filter is Whitman GFB glass filter paper. Controls include using samples which are known to contain ST receptors, e.g. intestinal membranes from rat intestine, human intestine, T84 cells, isolated ST receptor protein or cells expressing cloned nucleotide sequence encoding ST receptor proteins.

ST may be isolated from natural sources using standard techniques. Additionally, ST receptor binding peptides and conjugated compositions or portions thereof which are peptides may be prepared routinely by any of the following known techniques.

In addition to being conjugated to $^{125}$I, ST may be detectable by binding it to other radionuclides such as $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99}$mTc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi, $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, 191Os, $^{193M}$pt and $^{197}$Hg or by binding it to other labels such as fluorescein or enzymes. Each of the labelling means described above for detectably labelling antibodies can be adapted to label ST receptor ligands and are considered to be described as such herein.

Kits include containers comprising detectable ST receptor ligand together with containers having positive and/or negative controls, i.e. samples which contain ST receptor and samples which contain no ST receptor, respectively. The detectable ST receptor ligand is preferably labelled. Additional components in some kits include solid support, buffer, and instructions for carrying out the assay.

The ST receptor binding assay is useful for detecting ST receptor in homogenized tissue samples and body fluid samples including the plasma portion or cells in the fluid sample.

Nucleotide Sequence Based Detection:

Aspects of the present invention include various methods of determining whether a sample contains cells that express ST receptor by sequence-based molecular analysis. Several different methods are available for doing so including those using Polymerase Chain Reaction (PCR) technology such as PCR amplification including RT-PCR amplification, using Northern blot technology (mRNA), Southern Blot technology (cDNA), oligonucleotide hybridization technology, in situ hybridization technology, ribonuclease protection assay (RPA), in situ PCR or hybridization, S1-nuclease protection assay, immune-capture RT-PCR, nucleic acid sequence-based amplification (NASBA), branched DNA (bDNA) technology, and strand-displacement amplification (SDA).

The invention relates to oligonucleotide probes and primers used in the methods of identifying MRNA that encodes ST receptor and to diagnostic kits which comprise such components. In preferred embodiments, the probes and primers for detecting mRNA that encodes ST receptor protein preferably hybridize to nucleotide sequences that encode the extracellular domain (amino acids 24–430 encoded by nucleotides 72–1290) or the C terminal tail (amino acids 1031–1093 encoded by nucleotides 3091–3274) of ST receptor protein. Accordingly, the probes and primers for detecting mRNA that encodes ST receptor protein preferably hybridizes to nucleotide sequences within the sequence 72–1290 which is the sequence in the mRNA that encodes the extracellular domain (amino acids 24–430). Alternatively, the probes and primers for detecting mRNA that encodes ST receptor protein preferably hybridizes to nucleotide sequences within the sequence 3091–3274 which is the sequence in the mRNA that encodes the C terminal tail (amino acids 1031–1093) of ST receptor protein. The mRNA sequence-based methods for determining whether a sample mRNA encoding ST receptor include but are not limited to PCR amplification including RT-PCR amplification, Northern blot analysis of mRNA, Southern Blot analysis of cDNA generated from mRNA, oligonucleotide hybridization (dot blots), in situ hybridization, ribonuclease protection assays (RPA), in situ PCR or hybridization assays, S1-nuclease protection assays, immune-capture RT-PCR, nucleic acid sequence-based amplification (NASBA), branched DNA (bDNA) technology, and strand-displacement amplification (SDA).

The nucleotide sequence encoding ST receptor protein is well known such as in F. J. Sauvage et al. 1991 *J. Biol. Chem.* 266:17912–17918. In addition to being disclosed in Sauvage et al. SUPRA, the nucleotide sequence of human ST receptor is set forth herein as SEQ ID NO:1. Reagents, such as probes and primers which hybridize to mRNA or cDNA that encodes ST receptor protein, particularly reagents that hybridize to sequences within 72–1290 or 1031–1093 may be designed based upon sequence information in SEQ ID NO:1.

The methods described herein are meant to exemplify how the present invention may be practiced and are not meant to limit the scope of invention. It is contemplated that other sequence-based methodology for detecting the presence of specific mRNA that encodes ST receptor in extraintestinal amples may be employed according to the invention.

A preferred method to detecting mRNA that encodes ST eceptor in genetic material derived from extraintestinal samples uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR may be routinely practiced using Perkin Elmer Cetus GENE AMP RNA PCR kit, Part No. N808-0017.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

Primers are designed based upon the nucleotide sequence encoding ST receptor protein which is described in F. J. Sauvage et al. 1991 *J. Biol. Chem.* 266:17912–17918 and SEQ ID NO:1. Preferably, primers are designed to hybridize to sequences within 72–1290 of SEQ ID NO:1. In some embodiments, primers hybridize to sequences within 3091–3274 of SEQ ID NO:1. To perform this method, RNA is extracted from cells in a sample and tested or used to make cDNA using well known methods and readily available starting materials.

The mRNA or cDNA is combined with the primers, free nucleotides and enzyme following standard PCR protocols. The mixture undergoes a series of temperature changes. If the mRNA or cDNA encoding ST receptor is present, that is, if both primers hybridize to sequences on the same molecule, the molecule comprising the primers and the adjacent complementary sequences will be exponentially amplified. The amplified DNA can be easily detected by a variety of well known means. If the chimeric gene is not present, no DNA molecule will be exponentially amplified. Rather, amplification of wild-type transcript will yield low levels of variable length product. The PCR technology therefore provides an extremely easy, straightforward and reliable method of detecting mRNA encoding ST receptor protein in a sample.

PCR primers can be designed routinely by those having ordinary skill in the art using well known cDNA sequence information. Primers are generally 8–50 nucleotides, preferably 18–28 nucleotides. A set of primers contains two primers. When performing PCR on extracted mRNA or cDNA generated therefrom, if the mRNA or cDNA encoding ST receptor protein is present, multiple copies of the mRNA or cDNA will be made. If it is not present, PCR will not generate a discrete detectable product. Primers preferably hybridize to sequences within 72–1290 of SEQ ID NO:1 or sequences within 3091–3274 of SEQ ID NO:1. In some preferred embodiments primers selected from the group of SEQ ID NOs:3–72 are employed.

PCR product, i.e. amplified DNA, may be detected by several well known means. The preferred method for detecting the presence of amplified DNA is to separate the PCR reaction material by gel electrophoresis and stain the gel with ethidium bromide in order to visualize the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotide which are useful as primers for performing PCR methods to amplify mRNA or cDNA that encodes ST receptor protein.

According to the invention, diagnostic kits can be assembled which are useful to practice methods of detecting the presence of mRNA or cDNA that encodes ST receptor in extraintestinal samples. Such diagnostic kits comprise oligonucleotide which are useful as primers for performing PCR methods. In some preferred embodiments primers comprise sequences that hybridize to sequences within 72–1290 of SEQ ID NO:1 or sequences within 3091–3274 of SEQ ID NO:1. In some preferred embodiments, primers comprise sequences selected from the group SEQ ID NOs:3–72. It is preferred that diagnostic kits according to the present invention comprise a container comprising a size marker to be run as a standard on a gel used to detect the presence of amplified DNA. The size marker is the same size as the DNA generated by the primers in the presence of the mRNA or cDNA encoding ST receptor.

PCR assays are useful for detecting mRNA encoding ST receptor in homogenized tissue samples and cells in body fluid samples. It is contemplated that PCR on the plasma portion of a fluid sample could be used to detect mRNA encoding ST receptor protein.

Another method of determining whether a sample contains cells expressing ST receptor is by Northern Blot analysis of MRNA extracted from an extraintestinal sample. The techniques for performing Northern blot analyses are well known by those having ordinary skill in the art and are described in Sambrook, J. et al., (1989) *Molecular Cloning: A Laboratory Manual*, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

One having ordinary skill in the art, performing routine techniques, could design probes to identify mRNA encoding ST receptor using the information in F. J. Sauvage et al. 1991 *J. Biol. Chem.* 266:17912–17918. The sequence for human ST receptor is also disclosed in SEQ ID NO:1. In some preferred embodiments probes comprise sequences that hybridize to sequences within 1–1290 of SEQ ID NO:1 or sequences within 3091–3274 of SEQ ID NO:1.

The mRNA is extracted using poly dT columns and the material is separated by electrophoresis and, for example, transferred to nitrocellulose paper. Labelled probes made from an isolated specific fragment or fragments can be used to visualize the presence of a complementary fragment fixed to the paper.

According to the invention, diagnostic kits can be assembled which are useful to practice methods of detecting the presence of mRNA that encodes ST receptor in extraintestinal samples by Northern blot analysis. Such diagnostic kits comprise oligonucleotide which are useful as probes for hybridizing to the mRNA. The probes may be radiolabelled. In some preferred embodiments probes comprise sequences that hybridize to sequences within 72–1290 of SEQ ID NO:1 or sequences within 3091–3274 of SEQ ID NO:1. It is preferred that diagnostic kits according to the present invention comprise a container comprising a size marker to be run as a standard on a gel. It is preferred that diagnostic kits according to the present invention comprise a container comprising a positive control which will hybridize to the probe.

Northern blot analysis is useful for detecting mRNA encoding ST receptor in homogenized tissue samples and cells in body fluid samples. It is contemplated that PCR on the plasma portion of a fluid sample could be used to detect mRNA encoding ST receptor protein.

Another method of detecting the presence of mRNA encoding ST receptor protein by oligonucleotide hybridization technology. Oligonucleotide hybridization technology is well known to those having ordinary skill in the art. Briefly, detectable probes which contain a specific nucleotide sequence that will hybridize to nucleotide sequence of mRNA encoding ST receptor protein. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicates complementary sequences. One having ordinary skill in the art, using the sequence information disclosed in F. J. Sauvage et al. 1991 *J. Biol. Chem.* 266:17912–17918 and SEQ ID NO:1 can design probes which are fully complementary to mRNA sequences but not genomic DNA sequences. In some preferred embodiments probes comprise sequences that hybridize to sequences within 72–1290 of SEQ ID NO:1 or sequences within 3091–3274 of SEQ ID NO:1. Hybridization conditions can be routinely optimized to minimize background signal by non-fully complementary hybridization.

The present invention includes labelled oligonucleotide which are useful as probes for performing oligonucleotide hybridization. That is, they are fully complementary with mRNA sequences but not genomic sequences. For example, the mRNA sequence includes portions encoded by different exons. The labelled probes of the present invention are labelled with radiolabelled nucleotides or are otherwise detectable by readily available nonradioactive detection systems.

According to the invention, diagnostic kits can be assembled which are useful to practice oligonucleotide hybridization methods of the invention. Such diagnostic kits comprise a labelled oligonucleotide which encodes portions of ST receptor encoded by different exons. In some preferred embodiments probes comprise sequences that hybridize to sequences within 72–1290 of SEQ ID NO:1 or sequences within 3091–3274 of SEQ ID NO:1. It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

Oligonucleotide hybridization techniques are useful for detecting mRNA encoding ST receptor in homogenized tissue samples and cells in body fluid samples. It is contemplated that PCR on the plasma portion of a fluid sample could be used to detect mRNA encoding ST receptor protein.

Tissue Analysis:

Another aspect of the invention relates to methods of analyzing tissue samples which are fixed sections routinely prepared by surgical pathologists to characterize and evaluate cells. In some embodiments, the cells are from laminapropria and are analyzed to determine and evaluate the extent of metastasis of colorectal tumor cells. The laminapropria represents the barrier between the intestinal or colorectal track and the rest of the body. By identifying the presence of ST receptor or mRNA that encodes ST receptor protein in cells of the laminapropria, the extent of invasion/infiltration of colorectal tumor cells into extraintestinal tissue can be evaluated. In some embodiments, the cells are removed in a biopsy or as an adenocarcinoma of unknown origin and are analyzed to determine and evaluate whether they are colorectal tumor cells.

The present invention relates to in vitro kits for evaluating tissue samples to determine the level of metastasis and to reagents and compositions useful to practice the same. In some embodiments of the invention, tissue samples that include portions of the laminapropria may be isolated from individuals undergoing or recovering from surgery to remove colorectal tumors include resection or colonoscopy. The tissue is analyzed to identify the presence or absence of the ST receptor protein. Techniques such as an ST receptor/ligand binding assay and immunohistochemistry assay may be performed to determine whether the ST receptor is present in cells in the tissue sample which are indicative of metastatic migration. As discussed above, preferred immunoassays for identifying the presence of ST receptor protein use antibodies that bind to epitopes on ST receptor protein which comprise amino acids 24–430 or 1031–1093. Accordingly, in aspects of the invention which relate to immunohistochemistry assays and kits and reagents for performing the same, such extracellular domain-specific or C terminal tail-specific antibodies are preferred. Alternatively, in some embodiments of the invention, tissue samples are analyzed to identify whether ST receptor protein is being expressed in cells in the tissue sample which indicate metastatic migration by detecting the presence or absence of mRNA that encodes the ST receptor protein. The presence of mRNA that encodes the ST receptor protein or cDNA generated therefrom can be determined using techniques such as in situ hybridization and in situ PCR assays. The probes and primers used in in situ hybridization and in situ PCR assays preferably hybridize to sequence that encode amino acids 24–430 or amino acids 1031–1093 of ST receptor protein. Accordingly, in some preferred embodiments, probes comprise sequences that hybridize to sequences within 72–1290 of SEQ ID NO:1 or sequences within 3091–3274 of SEQ ID NO:1.

The present invention relates to in vitro kits for evaluating samples of tumors to determine whether or not they are colorectal in origin and to reagents and compositions useful to practice the same. In some embodiments of the invention, tumor samples may be isolated from individuals undergoing or recovering from surgery to remove tumors in the colon, tumors in other organs or biopsy material. The tumor sample is analyzed to identify the presence or absence of the ST receptor protein. Techniques such as an ST receptor/ligand binding assays and immunohistochemistry assays may be performed to determine whether the ST receptor is present in cells in the tumor sample which are indicative of colorectal origin. In some preferred embodiments of the invention which relate to immunohistochemistry assays and kits and reagents for performing the same, extracellular domain-specific antibodies (i.e. those which bind to epitopes on ST receptor protein which comprise amino acids 24–430) or C terminal tail-specific antibodies (amino acids 1031–1093) are preferred. Alternatively, in some embodiments of the invention, lumen tissue samples are analyzed to identify whether ST receptor protein is being expressed in cells in the tumor sample which indicate colorectal origin by detecting the presence or absence of mRNA that encodes the ST receptor protein. The presence of mRNA that encodes the ST receptor protein or cDNA generated therefrom can be determined using techniques such as in situ hybridization and in situ PCR assays. The probes and primers used in in situ hybridization and in situ PCR assays preferably hybridize to sequence that encode amino acids 24–430 or amino acids 1031–1093 of ST receptor protein. Accordingly, in some preferred embodiments, probes comprise sequences that hybridize to sequences within 72–1290 of SEQ ID NO:1 or sequences within 3091–3274 of SEQ ID NO:1.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them. One having ordinary skill in the art, using the sequence information in F. J. Sauvage et al. 1991 J. Biol. Chem. 266:17912–17918 and SEQ ID NO:1, can design probes useful in in situ hybridization technology to identify cells that express ST receptor. The probes used to detect in in situ hybridization preferably hybridize to sequence that encode amino acids 24–430 or amino acids 1031–1093 of ST receptor protein. Accordingly, in some preferred embodiments, probes comprise sequences that hybridize to sequences within 72–1290 of SEQ ID NO:1 or sequences within 3091–3274 of SEQ ID NO:1.

The probes are fully complementary and do not hybridize well to partially complementary sequences. For in situ hybridization according to the invention, it is preferred that the probes are detectable by fluorescence. A common procedure is to label probe with biotin-modified nucleotide and then detect with fluorescently tagged avidin. Hence, probe does not itself have to be labelled with florescent but can be subsequently detected with florescent marker.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences. It is preferred that labelled probes of the in situ diagnostic kits according to the present invention are labelled with a fluorescent marker.

Those having ordinary skill in the art can analyze the fixed cells to characterize the level of metastatic migration of the colon cancer cells. The labelling of colon-derived cells allows for improved analysis.

Immunohistochemistry techniques may be used to identify and essentially stain cells with ST receptor. Such "staining" allows for analysis of metastatic migration. Anti-ST receptor antibodies such as those described above of contacted with fixed cells and the ST receptor present in the cells reacts with the antibodies. The antibodies are detectably labelled or detected using labelled second antibody or protein A to stain the cells. In some preferred embodiments of the invention which relate to immunohistochemistry assays and kits and reagents for performing the same, extracellular domain-specific antibodies (i.e. those which bind to epitopes on ST receptor protein which comprise amino acids 72–430) or C terminal tail-specific antibodies (i.e. those which bind to epitopes on ST receptor protein which comprise amino acids 1031–1093) are preferred.

ST binding assays may be performed instead of immunohistochemistry except that the cell section is first frozen, then the ST binding assay is performed and then the cells are fixed.

The techniques described herein for evaluating tumor sections can also be used to analyze tissue sections for samples of lymph nodes as well as other tissues to identify the presence of colorectal tumor cells. The samples can be prepared and "stained" to detect expression of ST receptor.

EXAMPLE

ST receptor is a highly specific marker for metastatic colorectal cancer. The sequence of the human homologue of this protein has been defined and is shown in SEQ ID NO:1 and SEQ ID NO:2. Two human sequences have been defined, differing in only 2 amino acids in their extracellular binding domains. The differences include a conservative substitution of $C_{1038}$ and substitution of $C_{1039}$ to $G_{1039}$ with an associate conservative substitution of leu to val. The expression of ST receptor exclusively by metastatic colorectal cells, compared to other extraintestinal cells and tumors, permits detection of the presence of these cells in samples of tissues and body fluids by testing for the presence of the nucleic acids encoding this protein. Specifically, the presence of colorectal cancer cells expressing this marker can be detected by examining specimens for the presence of the ST receptor protein itself or the mRNA encoding this protein. This mRNA can be detected by a number of techniques involving the recognition and amplification of sequences in this mRNA which are unique for this protein compared to other proteins of this family or in general. For example, primers or oligonucleotides derived from specific sequences complimentary to the mRNA that encodes ST receptor can be used to detect the expression of this protein by PCR, RT-PCR, Northern blot analysis, RPA, in situ PCR or hybridization, S1-nuclease protection assay, immune-capture RT-PCR, nucleic acid sequence-based amplification (NASBA), branched DNA (bDNA) technology, and strand-displacement amplification (SDA).

According to some aspects of the invention, a key feature is the utility of specific sequences derived from specific sections of the DNA encoding this protein as probes for these techniques. Previous studies suggested that although ST receptor protein was primarily expressed in intestinal cells, there might be expression in other tissues as well, such as, for example, in brain and adrenal. However, the probes used in those studies for PCR or cDNA cloning were derived from the carboxy terminal domain of this protein. This domain shares significant sequence homology with almost all members of the family of particulate receptor guanylyl cyclases, of which there are currently 8 known members. In addition, comparing the probes used in those studies with existing gene data banks of known proteins demonstrated that the probes used in those earlier studies exhibited sufficient sequence homology to hybridize with >50 eukaryotic and prokaryotic proteins. In contrast, the extracellular domain of ST receptor protein (amino acids 24–430; nucleotides 72–1290) exhibits little sequence homology with other members of the guanylyl cyclase family (<10%) and no homology with other proteins. Thus, probes to examine the specific expression of ST receptor protein in tissues should ideally be derived from this unique region of the protein.

Recently, the expression of ST receptor protein in human tissues and tumors was examined employing cDNA probes complimentary to regions of the extracellular domain by RT-PCR and RNAase protection and compared these results to those employing probes used in earlier studies in which it was suggested that ST receptor protein might be expressed in other tissues. Indeed, using cDNA primers derived from the extracellular domain, the ST receptor protein was found to be expressed only in intestinal epithelial cells and colorectal cancer cells, but not in any other extraintestinal tissue or tumor, including brain and adrenal. In contrast, when the primers derived from the cytoplasmic domain of this protein were employed in the same RT-PCR experiments, complimentary mRNA was found in brain and adrenal, as demonstrated previously in other studies. These data, in which the unique extracellular domain is undetectable by PCR but the highly homologous cytoplasmic domain is detectable, in brain and adrenal, demonstrates that GCC is uniquely expressed only in intestinal epithelium cells and colorectal cancer cells but not in other extraintestinal tissues or tumors. In contrast, the PCR product detected in brain and adrenal employing primers derived from the cytoplasmic domain of ST receptor protein likely reflects a new member of the family of receptor guanylyl cyclases with homologous cytoplasmic domains.

These data demonstrate that the highest specificity for diagnostic tests employing ST receptor protein as a marker can be obtained with nucleotide sequences as test probes which are derived from the extracellular domain. Employing primers derived from the extracellular domain of ST receptor protein is a key feature of the diagnostic tests being developed for colorectal cancer.

A series of primers have been identified which are complimentary to various regions of the extracellular domain of human ST receptor protein. These primers were selected based on criteria of 100% specificity for the nucleotide sequence of interest (uniqueness for ST receptor protein) and optimization of hybridization compatibility (minimize non-specific. interactions and avoid significant secondary structure that may not permit hybridization). The utility of these sequences for identifying and amplifying ST receptor protein were confirmed by computer-based algorithms.

Primers are shown as SEQ ID NOs:3–72. Specific primer pairs include SEQ ID NO:3 and SEQ ID NO:4, SEQ ID NO:5 and SEQ ID NO:6, SEQ ID NO:7 and SEQ ID NO:8, SEQ ID NO:9 and SEQ ID NO:10, SEQ ID NO:11 and SEQ ID NO:12, SEQ ID NO:13 and SEQ ID NO:14, SEQ ID NO:15 and SEQ ID NO:16, SEQ ID NO:17 and SEQ ID NO:18, SEQ ID NO:19 and SEQ ID NO:20, SEQ ID NO:21 and SEQ ID NO:22, SEQ ID NO:23 and SEQ ID NO:24, SEQ ID NO:25 and SEQ ID NO:26, SEQ ID NO:27 and SEQ ID NO:28, SEQ ID NO:29 and SEQ ID NO:30, SEQ ID NO:31 and SEQ ID NO:32, SEQ ID NO:33 and SEQ ID NO:34, SEQ ID NO:35 and SEQ ID NO:36, SEQ ID NO:37 and SEQ ID NO:38, SEQ ID NO:39 and SEQ ID NO:40, SEQ ID NO:41 and SEQ ID NO:42, SEQ ID NO:43 and SEQ ID NO:44, SEQ ID NO:45 and SEQ ID NO:46, SEQ ID NO:47 and SEQ ID NO:48, SEQ ID NO:49 and SEQ ID NO:50, SEQ ID NO:51 and SEQ ID NO:52, SEQ ID NO:53 and SEQ ID NO:54, SEQ ID NO:55 and SEQ ID NO:56, SEQ ID NO:57 and SEQ ID NO:58, SEQ ID NO:59 and SEQ ID NO:60, SEQ ID NO:61 and SEQ ID NO:62, SEQ ID NO:63 and SEQ ID NO:64, SEQ ID NO:65 and SEQ ID NO:66, SEQ ID NO:67 and SEQ ID NO:68, SEQ ID NO:69 and SEQ ID NO:70, and SEQ ID NO:71 and SEQ ID NO:72.

The primers with odd numbered sequence identification numbers of SEQ ID NOs:3–72 (i.e. SEQ ID NO:3, SEQ ID NO:5, SEQ IN NO:7, etc.) can be matched with any of primers with even numbered sequence identification numbers of SEQ ID NOs:3–72 (i.e. SEQ ID NO:4, SEQ ID NO:6, SEQ IN NO:8, etc.) provided the pairing can be used to amplify a product from a template having SEQ ID NO:1. Those having ordinary skill in the art can readily identify which of the primers with odd numbered sequence identification numbers can be paired with which of primers with even numbered sequence identification numbers. For example, primers with odd numbered sequence identification numbers of SEQ ID NOs:3–49 SEQ ID NO:67 and SEQ ID NO:69 can be paired with any of primers with even numbered sequence identification numbers of SEQ ID NOs:3–72. Similarly, primers with SEQ ID NO:51, SEQ ID NO:63 and SEQ ID NO:65 can be paired with primers with SEQ ID NO:26, SEQ ID NO:32, SEQ ID NO:36, SEQ ID NO:46, even numbered sequence identification numbers of SEQ ID NOs:52–66 and SEQ ID NO:72. Primers with odd numbered sequence identification numbers SEQ ID NOs:53–57 can be paired with primers with even numbered sequence identification numbers of SEQ ID NOs:52–66 and SEQ ID NO:72. Primers with sequence identification numbers SEQ ID NO:59 and SEQ ID NO:61 can be paired with primers with even numbered sequence identification numbers of SEQ ID NOs:52–62 and SEQ ID NO:72. Primers with SEQ ID NO:71 can be paired with primers with SEQ ID NO:26, SEQ ID NO:32, SEQ ID NO:36, SEQ ID NO:46, even numbered sequence identification numbers of SEQ ID NOs:50–66 and SEQ ID NO:72.

Based on this selection, primers optimal for specific and sensitive detection of human ST receptor protein have been identified. These sequences are not only unique, highly specific, and cross-compatible, they are also free of non-specific dimer formation, secondary structures, and sequence repeats. PCR-generated hybridization probes generated with these primers will be exquisitely specific for signal-based amplification systems to detect expression of ST receptor protein, such as Northern analysis, ligase chain reaction (LCR), Q-beta replicase (QBR) assay, and bDNA. Various combinations of these primers have been successfully employed to specifically detect the expression of ST receptor protein in colorectal tumors in tissues and blood, compared to other extraintestinal tissues and tumors.

Alternate short sequence-specific antisense reverse transcription primers for amplification of the unique extracellular ligand binding domain of ST receptor protein may include SEQ ID NO:73 anbd/or SEQ ID NO:74.

This transmembrane domain of the human ST-receptor (hSTr) is 100% homologous between the hST-r sequences submitted to GENEBANK and EMBL. A series of 12–15 nucleotide antisense primers are generated from this sequence. Reverse transcription (RT) appears to be more specific and efficient using any of these short antisense RT-primers (Pfeffer U, Fecarotta E, Vidali G. (1995) Biotechniques 18:204–206 which is incorporated herein by reference). Indeed, multiplex short sequence-specific reverse transcription primers enhance specificity, due to the unique highly specific sequences selected, and their length prevents interference in subsequent amplification steps, due to their low melting temperatures. PCR and nested-PCR can then be used to identify any human ST-receptor sequences. This process is an alternative to employing the primers for RT-PCR described above.

What is claimed is:

1. An in vitro method of determining whether or not an individual has metastasized colorectal cancer cells comprising the steps of examining a sample of extraintestinal tissue and/or body fluids from an individual to determine whether ST receptor protein is being expressed by cells in said sample; wherein expression of ST receptor protein is determined by detecting the presence of mRNA in said sample that encodes amino acids 24–430 of human ST receptor protein, wherein:

said human ST receptor protein is SEQ ID NO:2; and expression of said ST receptor protein by said cells is determined by polymerase chain reaction, wherein said sample is contacted with primers that selectively amplify mRNA or cDNA that encodes the ST receptor protein, wherein at least one of said primers hybridizes to sequences that encode amino acids 24–430 of human ST receptor protein; and wherein at least one primer consists of a nucleic acid sequence selected from the group consisting of: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, and SEQ ID NO:72.

2. The method of claim 1 wherein said primers are a pair of primers selected from the group consisting of: SEQ ID NO:3 and SEQ ID NO:4; SEQ ID NO:5 and SEQ ID NO:6; SEQ ID NO:7 and SEQ ID NO:8; SEQ ID NO:9 and SEQ IDNO:10; SEQ ID NO:11 and SEQ ID NO:12; SEQ ID NO:13 and SEQ IDNO:14; SEQ IDNO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:33 and SEQ ID NO:34; SEQ ID NO:35 and SEQ ID NO:36; SEQ ID NO:37 and SEQ ID NO:38; SEQ ID NO:39 and SEQ ID NO:40; SEQ ID NO:41 and SEQ ID NO:42; SEQ ID NO:43 and SEQ ID NO:44; SEQ ID NO:45 and SEQ ID NO:46; SEQ ID NO:47 and SEQ ID NO:48; SEQ ID NO:49 and SEQ ID NO:50; SEQ ID NO:51 and SEQ ID NO:52; SEQ ID NO:53 and SEQ ID NO:54; SEQ ID NO:55 and SEQ ID NO:56; SEQ ID NO:57 and SEQ ID NO:58; SEQ ID NO:59 and SEQ ID NO:60; SEQ ID NO:61 and SEQ ID NO:62; SEQ ID NO:63 and SEQ ID NO:64; SEQ ID NO:65 and SEQ ID NO:66; SEQ ID NO:67 and SEQ ID NO:68; SEQ ID NO:69 and SEQ ID NO:70; and SEQ ID NO:71 and SEQ ID NO:72.

3. The method of claim 1 wherein the individual has been previously diagnosed as having primary colorectal cancer.

4. An in vitro method of determining whether or not a tumor cell is a colorectal tumor cell comprising the steps of determining whether said tumor cell expresses ST receptor protein; wherein expression of ST receptor protein in a sample of tumor cells is determined by detecting the presence of mRNA that encodes amino acids 24–430 of human ST receptor protein, wherein:

said human ST receptor protein is SEQ ID NO:2; and expression of said ST receptor protein by said cells is determined by polymerase chain reaction, wherein said sample is contacted with primers that selectively amplify mRNA or cDNA that encodes the ST receptor protein, wherein at least one of said primers hybridizes to sequences that encode amino acids 24–430 of the human ST receptor protein; and wherein at least one primer consists of a nucleic acid sequence selected from the group consisting of: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, and SEQ ID NO:72.

5. The method of claim 4 wherein said primers are a pair of primers selected from the group consisting of: SEQ ID NO:3 and SEQ ID NO:4; SEQ ID NO:5 and SEQ ID NO:6;

SEQ ID NO:7 and SEQ ID NO:8; SEQ ID NO:9 and SEQ ID NO:10; SEQ ID NO:11 and SEQ ID NO:12; SEQ ID NO:13 and SEQ ID NO:14; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:33 and SEQ ID NO:34; SEQ ID NO:35 and SEQ ID NO:36; SEQ ID NO:37 and SEQ ID NO:38; SEQ ID NO:39 and SEQ ID NO:40; SEQ ID NO:41 and SEQ ID NO:42; SEQ ID NO:43 and SEQ ID NO:44; SEQ ID NO:45 and SEQ ID NO:46; SEQ ID NO:47 and SEQ ID NO:48; SEQ ID NO:49 and SEQ ID NO:50; SEQ ID NO:51 and SEQ ID NO:52; SEQ ID NO:53 and SEQ ID NO:54; SEQ ID NO:55 and SEQ ID NO:56; SEQ ID NO:57 and SEQ ID NO:58; SEQ ID NO:59 and SEQ ID NO:60; SEQ ID NO:61 and SEQ ID NO:62; SEQ ID NO:63 and SEQ ID NO:64; SEQ ID NO:65 and SEQ ID NO:66; SEQ ID NO:67 and SEQ ID NO:68; SEQ ID NO:69 and SEQ ID NO:70; and SEQ ID NO:71 and SEQ ID NO:72.

6. The method of claim 4 wherein the tumor cell sample was obtained from an individual who was previously diagnosed as having primary colorectal cancer.

7. An in vitro method of screening an individual for metastasized colorectal cancer comprising the step of examining a sample of extraintestinal tissue from an individual to detect the presence of mRNA that encodes ST receptor protein in said sample; wherein the presence of mRNA that encodes the ST receptor protein is detected by detecting the presence of mRNA that encodes amino acids 24–430 of human ST receptor protein, wherein:

said human ST receptor protein is SEQ ID NO:2; and expression of said ST receptor protein by said cells is determined by polymerase chain reaction, wherein said sample is contacted with primers that selectively amplify mRNA or cDNA that encodes the ST receptor protein, wherein at least one of said primers hybridizes to sequences that encode amino acids 24–430 of the human ST receptor protein; and wherein at least one primer consists of a nucleic acid sequence selected from the group consisting of: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, and SEQ ID NO:72.

8. The method of claim 7 wherein said primers are a pair of primers selected from the group consisting of: SEQ ID NO:3 and SEQ ID NO:4; SEQ ID NO:5 and SEQ ID NO:6; SEQ ID NO:7 and SEQ ID NO:8; SEQ ID NO:9 and SEQ ID NO:10; SEQ ID NO:11 and SEQ ID NO:12; SEQ ID NO:13 and SEQ ID NO:14; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:33 and SEQ ID NO:34; SEQ ID NO:35 and SEQ ID NO:36; SEQ ID NO:37 and SEQ ID NO:38; SEQ ID NO:39 and SEQ ID NO:40; SEQ ID NO:41 and SEQ ID NO:42; SEQ ID NO:43 and SEQ ID NO:44; SEQ ID NO:45 and SEQ ID NO:46; SEQ ID NO:47 and SEQ ID NO:48; SEQ ID NO:49 and SEQ ID NO:50; SEQ ID NO:51 and SEQ ID NO:52; SEQ ID NO:53 and SEQ ID NO:54; SEQ ID NO:55 and SEQ ID NO:56; SEQ ID NO:57 and SEQ ID NO:58; SEQ ID NO:59 and SEQ ID NO:60; SEQ ID NO:61 and SEQ ID NO:62; SEQ ID NO:63 and SEQ ID NO:64; SEQ ID NO:65 and SEQ ID NO:66; SEQ ID NO:67 and SEQ ID NO:68; SEQ ID NO:69 and SEQ ID NO:70; and SEQ ID NO:71 and SEQ ID NO:72.

9. The method of claim 7 wherein the individual has been previously diagnosed as having primary colorectal cancer.

10. An in vitro method of screening an individual for metastasized colorectal cancer comprising the step of examining a sample of extraintestinal body fluids from an individual to detect the presence of mRNA that encodes ST receptor protein in said sample; wherein the presence of mRNA that encodes the ST receptor protein is detected by detecting the presence of mRNA that encodes amino acids 24–430 of human ST receptor protein, wherein:

said human ST receptor protein is SEQ ID NO:2; and expression of said ST receptor protein by said cells is determined by polymerase chain reaction, wherein said sample is contacted with primers that selectively amplify mRNA or cDNA that encodes the ST receptor protein, wherein at least one of said primers hybridizes to sequences that encode amino acids 24–430 of the human ST receptor protein; and wherein at least one primer consists of a nucleic acid sequence selected from the group consisting of: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, and SEQ ID NO:72.

11. The method of claim 10 wherein said primers are a pair of primers selected from the group consisting of: SEQ ID NO:3 and SEQ ID NO:4; SEQ ID NO:5 and SEQ ID NO:6; SEQ ID NO:7 and SEQ ID NO:8; SEQ ID NO:9 and SEQ ID NO:10; SEQ ID NO:11 and SEQ ID NO:12; SEQ ID NO:13 and SEQ ID NO:14; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:33 and SEQ ID NO:34; SEQ ID NO:35 and SEQ ID NO:36; SEQ ID NO:37 and SEQ ID NO:38; SEQ ID NO:39 and SEQ ID NO:40; SEQ ID NO:41 and SEQ ID NO:42; SEQ ID NO:43 and SEQ ID NO:44; SEQ ID NO:45 and SEQ ID NO:46; SEQ ID NO:47 and SEQ ID NO:48; SEQ ID NO:49 and SEQ ID NO:50; SEQ ID NO:51 and SEQ ID NO:52; SEQ ID NO:53 and SEQ ID NO:54; SEQ ID NO:55 and SEQ ID NO:56; SEQ ID NO:57 and SEQ ID NO:58; SEQ ID NO:59 and SEQ ID NO:60; SEQ ID NO:61 and SEQ ID NO:62; SEQ ID NO:63 and SEQ ID NO:64; SEQ ID NO:65 and SEQ ID NO:66; SEQ ID NO:67 and SEQ ID NO:68; SEQ ID NO:69 and SEQ ID NO:70; and SEQ ID NO:71 and SEQ ID NO:72.

12. The method of claim 10 wherein the individual has been previously diagnosed as having primary colorectal cancer.

\* \* \* \* \*